United States Patent
Akkus et al.

(10) Patent No.: US 11,937,973 B2
(45) Date of Patent: Mar. 26, 2024

(54) SYSTEMS AND MEDIA FOR AUTOMATICALLY DIAGNOSING THYROID NODULES

(71) Applicant: Mayo Foundation for Medical Education and Research, Rochester, MN (US)

(72) Inventors: Zeynettin Akkus, Rochester, MN (US); Bradley J. Erickson, Rochester, MN (US); Matthew R. Callstrom, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 519 days.

(21) Appl. No.: 17/058,871

(22) PCT Filed: May 31, 2019

(86) PCT No.: PCT/US2019/034870
§ 371 (c)(1),
(2) Date: Nov. 25, 2020

(87) PCT Pub. No.: WO2019/232346
PCT Pub. Date: Dec. 5, 2019

(65) Prior Publication Data
US 2021/0219944 A1    Jul. 22, 2021

Related U.S. Application Data

(60) Provisional application No. 62/678,736, filed on May 31, 2018.

(51) Int. Cl.
*A61B 8/08*        (2006.01)
*G06N 3/045*       (2023.01)
*G06N 3/084*       (2023.01)

(52) U.S. Cl.
CPC .............. *A61B 8/085* (2013.01); *A61B 8/485* (2013.01); *A61B 8/488* (2013.01); *A61B 8/5223* (2013.01); *G06N 3/045* (2023.01); *G06N 3/084* (2013.01)

(58) Field of Classification Search
CPC ......... A61B 8/085; A61B 8/485; A61B 8/488; A61B 8/5223; G06N 3/045; G06N 3/084; G16H 50/30
See application file for complete search history.

(56) References Cited

U.S. PATENT DOCUMENTS 7,022,077 B2    4/2006   Mourad
9,589,374 B1    3/2017   Gao
(Continued)

FOREIGN PATENT DOCUMENTS

CN    106056595 A    10/2016
CN    106780448 A    5/2017
(Continued)

OTHER PUBLICATIONS

Li et al., CNN Architechtures, Lecture 9, May 2, 2017.*
(Continued)

*Primary Examiner* — Bo Joseph Peng
(74) *Attorney, Agent, or Firm* — Quarles & Brady LLP

(57) ABSTRACT

In accordance with some embodiments, systems, methods, and media for automatically localizing and diagnosing thyroid nodules are provided. In some embodiments, a system for automatically diagnosing thyroid nodules comprises: an ultrasound machine; and a processor programmed to: receive a B-mode ultrasound of a thyroid from the ultrasound machine; provide the B-mode ultrasound to a classification model trained to automatically segment B-mode ultrasound; receive an output indicating which portions of the B-mode ultrasound correspond to a nodule; provide at (Continued)

least a portion of the B-mode ultrasound corresponding to the nodule to a second classification model trained to automatically classify thyroid nodules based B-mode, color Doppler, and shear wave elastography ultrasound; and receive, from the second trained classification model, an output indicative of the likelihood that the nodule is malignant.

20 Claims, 14 Drawing Sheets

(56) References Cited

U.S. PATENT DOCUMENTS

| | | | |
|---|---|---|---|
| 2012/0201445 A1 | 8/2012 | El-Baz | |
| 2012/0220875 A1* | 8/2012 | Suri | G16H 70/60 600/407 |
| 2018/0240235 A1* | 8/2018 | Mazo | G06T 7/11 |
| 2019/0012170 A1* | 1/2019 | Qadeer | G06N 3/045 |

FOREIGN PATENT DOCUMENTS

| | | |
|---|---|---|
| CN | 107369154 A | 11/2017 |
| CN | 107480691 A | 12/2017 |

OTHER PUBLICATIONS

Acharya, U. R. et al. Automated benign & malignant thyroid lesion characterization and classification in 3D contrast-enhanced ultrasound. in 2012 Annual International Conference of the IEEE Engineering in Medicine and Biology Society 452-455 (2012).
Akkus, Z. et al. Deep Learning for Brain MRI Segmentation: State of The Art and Future Directions. Journal of digital imaging 30.4 (2017): 449-459.
Akkus, Z. et al. Predicting Deletion of Chromosomal Arms 1p/19q in Low-Grade Gliomas from MR Images Using Machine Intelligence. J. Digit. Imaging 30, 469-476 (2017).
Akkus, Z. et al. Reduction of unnecessary thyroid biopsies using deep learning. Medical Imaging 2019: Image Processing. vol. 10949. International Society for Optics and Photonics, 2019.
Banzato, T., et al. "Use of transfer learning to detect diffuse degenerative hepatic diseases from ultrasound images in dogs: a methodological study." The Veterinary Journal 233 (Jan. 2018): 35-40.
Burman, K. D. et al. Thyroid Nodules. N. Engl. J. Med. 373, 2347-2356 (2015).
Chi, J. et al. Thyroid Nodule Classification in Ultrasound Images by Fine-Tuning Deep Convolutional Neural Network. J. Digit. Imaging 30, 477-486 (2017).
Cooper, DS et al. American Thyroid Association (ATA) Guidelines Taskforce on Thyroid Nodules and Differentiated Thyroid Cancer et al. Revised American Thyroid Association management guidelines for patients with thyroid nodules and differentiated thyroid cancer. Thyroid 19, 1167-1214 (2009).
Ding, J., et al. Quantitative Measurement for Thyroid Cancer Characterization Based on Elastography. J. Ultrasound Med. 30, 1259-1266 (2011).
Frates, M. C. et al. Management of thyroid nodules detected at US: Society of Radiologists in Ultrasound consensus conference statement. Ultrasound Q. 22, 231-8; discussion 239-40 (2006).
Gregory, A., et al. "Differentiation of benign and malignant thyroid nodules by using comb-push ultrasound shear elastography: a preliminary two-plane view study." Academic radiology 25.11 (Mar. 2018): 1388-1397.
Guille, J. T., et al. Evaluation and management of the pediatric thyroid nodule. Oncologist 20, 19-27 (2015).
He, K., et al. Deep residual learning for image recognition. in Proceedings of the IEEE conference on computer vision and pattern recognition 770-778 (2016).

Hegedus, L. The Thyroid Nodule. N. Engl. J. Med. 351, 1764-1771 (2004).
Huynh et al., "Digital Mammographic Tumor Classification using Transfer Learning from Deep Convolution Neural Networks," Journal of Medical Imaging, Jul. 2016, vol. 3, Iss. 3.
Huynh, B., et al. "MO-DE-207B-06: Computer-aided diagnosis of breast ultrasound images using transfer learning from deep convolutional neural networks." Medical physics 43.6Part30 (2016): 3705-3705.
Inoue, K., et al. "Computer aided detection of breast cancer on ultrasound imaging using deep learning." Ultrasound in Medicine and Biology 43 (2017): S19.
International Searching Authority. International Search Report and Written Opinion for application PCT/US2019/034870, dated Aug. 12, 2019. 19 pages.
Jemal, A. et al. Cancer statistics, 2005. CA Cancer J. Clin. 55, 10-30 (2005).
Khachnaoui, H. et al. "A review on deep learning in thyroid ultrasound computer-assisted diagnosis systems." 2018 IEEE International Conference on Image Processing, Applications and Systems (IPAS). pp. 291-297. IEEE, Dec. 2018.
Kuo, S-J., et al. "Classification of benign and malignant breast tumors using neural networks and three-dimensional power Doppler ultrasound." Ultrasound in Obstetrics and Gynecology: The Official Journal of the International Society of Ultrasound in Obstetrics and Gynecology 32.1 (2008): 97-102.
Li, X. et al. Diagnosis of thyroid cancer using deep convolutional neural network models applied to sonographic images: a retrospective, multicohort, diagnostic study. Lancet Oncol. (Dec. 2018). doi:10.1016/S1470-2045(18) 30762-9.
Liu, T., et al. "Feature selection and thyroid nodule classification using transfer learning." 2017 IEEE 14th International Symposium on Biomedical Imaging (ISBI 2017). IEEE, 2017.
Liu, T., et al. Classification of thyroid nodules in ultrasound images using deep model based transfer learning and hybrid features. in 2017 IEEE International Conference on Acoustics, Speech and Signal Processing (ICASSP) (2017). doi:10.1109/icassp.2017. 7952290.
Ma et al., "A Pre-trained Convolutional Neural Network Based Method for Thyroid Nodule Diagnosis," Ultrasonics, Jan. 2017, vol. 73, pp. 221-230.
Ma et al., "Ultrasound Image-based Thyroid Nodule Automatic Segmentation using Convolutional Neural Networks," International Journal of Computer Assisted Radiology and Surgery, Nov. 2017, vol. 12, Iss. 11, pp. 1895-1910.
Ma, J., et al. "Cascade convolutional neural networks for automatic detection of thyroid nodules in ultrasound images." Medical physics 44.5 (2017): 1678-1691.
McQueen, A. S. et al. Thyroid nodule ultrasound: technical advances and future horizons. Insights Imaging 6, 173-188 (2015).
Niyaz, U. et al. "Advances in deep learning techniques for medical image analysis." 2018 Fifth International Conference on Parallel, Distributed and Grid Computing (PDGC). 271-277. IEEE, Dec. 2018.
Papini, "Risk of Malignancy in Nonpalpable Thyroid Nodules: Predictive Value of Ultrasound and Color-Doppler Features," J. Clin. Endocrinol. Metab., vol. 87, No. 5, pp. 1941-1946, 2002.
Pereira, C. et al. "Comparison of machine learned approaches for thyroid nodule characterization from shear wave elastography images." Medical Imaging 2018: Computer-Aided Diagnosis. vol. 10575. International Society for Optics and Photonics, Feb. 2018.
Ronneberger et al., "U-Net: Convolutional Networks for Biomedical Image Segmentation," available at arxiv(dot)org/abs/1505. 04597 (2015).
Rouhi, R., et al. "Benign and malignant breast tumors classification based on region growing and CNN segmentation." Expert Systems with Applications 42.3 (2015): 990-1002.
Sollini, M., et al. Texture analysis and machine learning to characterize suspected thyroid nodules and differentiated thyroid cancer: Where do we stand? Eur. J. Radiol. 99, 1-8 (Feb. 2018).
Szegedy, C., et al. Rethinking the inception architecture for computer vision. in Proceedings of the IEEE Conference on Computer Vision and Pattern Recognition 2818-2826 (2016).

(56) References Cited

OTHER PUBLICATIONS

Tajbakhsh, N., et al. "Convolutional Neural Networks for Medical Image Analysis: Full Training or Fine Tuning?." arxiv.org, 2016. Cornell University Library, 201 Olin Library Cornell University, Ithaca, NY 14853.
Tsantis, S., et al. Morphological and wavelet features towards sonographic thyroid nodules evaluation. Comput. Med. Imaging Graph. 33, 91-99 (2009).
Weng, S., et al. "Combining deep learning and coherent anti-Stokes Raman scattering imaging for automated differential diagnosis of lung cancer." Journal of biomedical optics 22.10 (2017): 106017.
Yu, Q., et al. "Computer-aided diagnosis of malignant or benign thyroid nodes based on ultrasound images." European Archives of Oto-rhino-laryngology 274.7 (2017): 2891-2897.
Zhang et al., "Shear wave elastography for differentiation of benign and malignant thyroid nodules: a meta-analysis," J. Ultrasound Med., vol. 32, No. 12, pp. 2163-2169, Dec. 2013.

\* cited by examiner

RESNET

| layer name | output size | 18-layer | 34-layer | 50-layer | 101-layer | 152-layer |
|---|---|---|---|---|---|---|
| conv1 | 112×112 | 7×7, 64, stride 2 | | | | |
| conv2_x | 56×56 | 3×3 max pool, stride 2 | | | | |
| | | $\begin{bmatrix} 3\times3, 64 \\ 3\times3, 64 \end{bmatrix} \times 2$ | $\begin{bmatrix} 3\times3, 64 \\ 3\times3, 64 \end{bmatrix} \times 3$ | $\begin{bmatrix} 1\times1, 64 \\ 3\times3, 64 \\ 1\times1, 256 \end{bmatrix} \times 3$ | $\begin{bmatrix} 1\times1, 64 \\ 3\times3, 64 \\ 1\times1, 256 \end{bmatrix} \times 3$ | $\begin{bmatrix} 1\times1, 64 \\ 3\times3, 64 \\ 1\times1, 256 \end{bmatrix} \times 3$ |
| conv3_x | 28×28 | $\begin{bmatrix} 3\times3, 128 \\ 3\times3, 128 \end{bmatrix} \times 2$ | $\begin{bmatrix} 3\times3, 128 \\ 3\times3, 128 \end{bmatrix} \times 4$ | $\begin{bmatrix} 1\times1, 128 \\ 3\times3, 128 \\ 1\times1, 512 \end{bmatrix} \times 4$ | $\begin{bmatrix} 1\times1, 128 \\ 3\times3, 128 \\ 1\times1, 512 \end{bmatrix} \times 4$ | $\begin{bmatrix} 1\times1, 128 \\ 3\times3, 128 \\ 1\times1, 512 \end{bmatrix} \times 8$ |
| conv4_x | 14×14 | $\begin{bmatrix} 3\times3, 256 \\ 3\times3, 256 \end{bmatrix} \times 2$ | $\begin{bmatrix} 3\times3, 256 \\ 3\times3, 256 \end{bmatrix} \times 6$ | $\begin{bmatrix} 1\times1, 256 \\ 3\times3, 256 \\ 1\times1, 1024 \end{bmatrix} \times 6$ | $\begin{bmatrix} 1\times1, 256 \\ 3\times3, 256 \\ 1\times1, 1024 \end{bmatrix} \times 23$ | $\begin{bmatrix} 1\times1, 256 \\ 3\times3, 256 \\ 1\times1, 1024 \end{bmatrix} \times 36$ |
| conv5_x | 7×7 | $\begin{bmatrix} 3\times3, 512 \\ 3\times3, 512 \end{bmatrix} \times 2$ | $\begin{bmatrix} 3\times3, 512 \\ 3\times3, 512 \end{bmatrix} \times 3$ | $\begin{bmatrix} 1\times1, 512 \\ 3\times3, 512 \\ 1\times1, 2048 \end{bmatrix} \times 3$ | $\begin{bmatrix} 1\times1, 512 \\ 3\times3, 512 \\ 1\times1, 2048 \end{bmatrix} \times 3$ | $\begin{bmatrix} 1\times1, 512 \\ 3\times3, 512 \\ 1\times1, 2048 \end{bmatrix} \times 3$ |
| | 1×1 | average pool, 1000-d fc, softmax | | | | |
| FLOPs | | $1.8\times10^9$ | $3.6\times10^9$ | $3.8\times10^9$ | $7.6\times10^9$ | $11.3\times10^9$ |

FIG. 7

Transverse Images

Longitudinal Images

| Model | InceptionV3 | | | | Resnet50 | | | |
|---|---|---|---|---|---|---|---|---|
| Input | Image Only | | Image with Attention Map | | Image Only | | Image with Attention Map | |
| Dataset | Validation | Test | Validation | Test | Validation | Test | Validation | Test |
| Sensitivity | 0.9 | 0.86 | 0.8 | 0.86 | 0.75 | 0.86 | 0.7 | 0.84 |
| Specificity | 0.85 | 0.76 | 0.95 | 0.9 | 0.95 | 0.78 | 0.85 | 0.84 |
| PPV | 0.85 | 0.78 | 0.94 | 0.9 | 0.94 | 0.8 | 0.82 | 0.84 |
| NPV | 0.89 | 0.84 | 0.82 | 0.87 | 0.79 | 0.85 | 0.74 | 0.84 |
| AUC | 0.87 | 0.81 | 0.88 | 0.88 | 0.85 | 0.82 | 0.78 | 0.84 |

SYSTEMS AND MEDIA FOR AUTOMATICALLY DIAGNOSING THYROID NODULES

CROSS-REFERENCE TO RELATED APPLICATIONS

This application a 371 U.S. National Phase Entry of International Application No. PCT/US2019/034870, filed May 31, 2019, which claims the benefit of U.S. Provisional Patent Application No. 62/678,736, filed May 31, 2018, which. Each of the preceding patent applications is hereby incorporated herein by reference in its entirety for all purposes.

STATEMENT REGARDING FEDERALLY SPONSORED RESEARCH

N/A

BACKGROUND

Thyroid nodules are extremely common lesions that are found in 4-8% of adults by manual examination (e.g., palpation), 19-67% through examination of thyroid ultrasound (US) images, and 50% through examination via autopsy. Currently, the only non-surgical test that has proven to reliably differentiate a benign from a malignant nodule is fine needle aspiration (FNA). US has become an important diagnostic tool in the assessment of thyroid nodules, as it is safe and highly sensitive for detecting nodules. Additionally, sonographic features of the nodules may be suitable to assist a physician making a determination of whether an FNA is needed. Studies have shown that the overall incidence of cancer in patients with thyroid nodules selected for FNA is only 9.2-13.0%. Accordingly, there is a clinical need for a dramatic reduction of unnecessary FNA biopsies.

An ultrasound based detection and classification system that achieves high positive predictive value and specificity for malignancy could reduce unnecessary biopsies.

Accordingly, systems, methods, and media for automatically diagnosing thyroid nodules are desirable.

SUMMARY

In accordance with some embodiments of the disclosed subject matter, systems, methods, and media for automatically diagnosing thyroid nodules are provided.

In accordance with some embodiments of the disclosed subject matter, a system for automatically diagnosing thyroid nodules is provided, the system comprising: at least one hardware processor that is programmed to: receive a B-mode ultrasound image of a subject's thyroid; provide the B-mode ultrasound image to a first trained classification model, wherein the first trained classification model was trained to automatically segment B-mode ultrasound images based on manually segmented B-mode ultrasound images; receive, from the first trained classification model, an output indicating which portions of the B-mode ultrasound image correspond to a nodule; provide at least a portion of the B-mode ultrasound image corresponding to the nodule to a second trained classification model, wherein the second trained classification model was trained to automatically classify thyroid nodules based on manually labeled portions of B-mode ultrasound image data, color Doppler ultrasound image data, and shear wave elastography ultrasound image data corresponding to benign and malignant nodules; and receive, from the second trained classification model, an output indicative of a likelihood that the nodule is malignant.

In some embodiments, the system further comprises: an ultrasound machine configured to output B-mode image data; and the at least one hardware processor is further programmed to receive the B-mode ultrasound image from the ultrasound machine.

In some embodiments, the at least one hardware processor is further programmed to: receive a color Doppler ultrasound image of the subject's thyroid; provide at least a portion of the color Doppler ultrasound image corresponding to the nodule to the second trained classification model; receive a shear wave elastography ultrasound image of the subject's thyroid; provide at least a portion of the shear wave elastography ultrasound image corresponding to the nodule to the second trained classification model; and receive, from the second trained classification model, the output indicative of the likelihood that the nodule is malignant based on the information included in the B-mode ultrasound image, the color Doppler ultrasound image, and the shear wave elastography ultrasound image.

In some embodiments, the at least one hardware processor is further programmed to: concurrently provide at least the portion of the B-mode ultrasound image on a first input channel of the second trained classification model, at least the portion of the color Doppler ultrasound image on a second input channel of the second trained classification model, and at least the portion of the shear wave elastography ultrasound image on a third input channel of the second trained classification model.

In some embodiments, the at least one hardware processor is further programmed to: automatically segment the color Doppler ultrasound image based on the segmentation of the B-mode ultrasound image.

In some embodiments, the at least one hardware processor is further programmed to: automatically segment the shear wave elastography ultrasound image based on the segmentation of the B-mode ultrasound image.

In some embodiments, the at least one hardware processor is further programmed to: receive, from the first trained classification model, a mask indicating which pixels of the B-mode ultrasound image correspond to the nodule.

In some embodiments, the at least one hardware processor is further programmed to: provide the mask as an input to the second trained classification model.

In some embodiments, the first trained classification model is a convolutional neural network with an architecture based on U-Net.

In some embodiments, the second trained classification model is a convolutional neural network with an architecture based on Resnet 50.

In some embodiments, the second trained classification model is a convolutional neural network with an architecture based on InceptionV3.

In some embodiments, the second trained classification model is configured to classify nodules into a first class and a second class, the first class corresponding to benign nodules and the second class corresponding to malignant nodules.

In some embodiments, the output of the second trained classification model comprises a first confidence value corresponding to a likelihood that the nodule is a member of the first class, and a second confidence value corresponding to a likelihood that the nodule is a member of the second class.

In some embodiments, the at least one hardware processor is further programmed to: indicate that the nodule is benign in response to the first confidence value corresponds to a 100% confidence that the nodule is an example of the first class.

In accordance with some embodiments of the disclosed subject matter, a method for automatically diagnosing thyroid nodules is provided, the method comprising: receiving a B-mode ultrasound image of a subject's thyroid; providing the B-mode ultrasound image to a first trained classification model, wherein the first trained classification model was trained to automatically segment B-mode ultrasound images based on manually segmented B-mode ultrasound images; receiving, from the first trained classification model, an output indicating which portions of the B-mode ultrasound image correspond to a nodule; providing at least a portion of the B-mode ultrasound image corresponding to the nodule to a second trained classification model, wherein the second trained classification model was trained to automatically classify thyroid nodules based on manually labeled portions of B-mode ultrasound image data, color Doppler ultrasound image data, and shear wave elastography ultrasound image data corresponding to benign and malignant nodules; and receiving, from the second trained classification model, an output indicative of a likelihood that the nodule is malignant.

In accordance with some embodiments of the disclosed subject matter, a system for automatically diagnosing thyroid nodules, the system comprising: at least one hardware processor that is programmed to: receive a B-mode ultrasound image of a subject's thyroid; receive information indicating which portions of the B-mode ultrasound correspond to a nodule; provide at least a portion of the B-mode ultrasound image corresponding to the nodule to a second trained classification model, wherein the second trained classification model was trained to automatically classify thyroid nodules based on a plurality of B-mode ultrasound images each labeled as including a benign nodule of a malignant nodule; and receive, from the second trained classification model, an output indicative of a likelihood that the nodule is malignant.

In some embodiments, the system further comprises: an ultrasound machine configured to output B-mode image data; and the at least one hardware processor is further programmed to receive the B-mode ultrasound image from the ultrasound machine.

In some embodiments, the at least one hardware processor is further programmed to: provide at least the portion of the B-mode ultrasound image on a first input channel of the second trained classification model, and the information indicating which portions of the B-mode ultrasound correspond to the nodule on a second input channel of the second trained classification model.

In some embodiments, the information indicating which portions of the B-mode ultrasound correspond to the nodule comprises a mask indicating which pixels of the B-mode ultrasound image correspond to the nodule.

In some embodiments, the at least one hardware processor is further programmed to: provide the mask as an input to the second trained classification model.

In some embodiments, the at least one hardware processor is further programmed to: provide the B-mode ultrasound image to a first trained classification model, wherein the first trained classification model was trained to automatically segment B-mode ultrasound images based on manually segmented B-mode ultrasound images; and receive, from the first trained classification model, the mask.

In some embodiments, the second trained classification model is a convolutional neural network with an architecture based on Resnet 50.

In some embodiments, the second trained classification model is a convolutional neural network with an architecture based on InceptionV3.

In some embodiments, the second trained classification model is configured to classify nodules into a first class and a second class, the first class corresponding to benign nodules and the second class corresponding to malignant nodules.

In some embodiments, the output of the second trained classification model comprises a first confidence value corresponding to a likelihood that the nodule is a member of the first class, and a second confidence value corresponding to a likelihood that the nodule is a member of the second class.

In some embodiments, the at least one hardware processor is further programmed to: indicate that the nodule is benign in response to the first confidence value corresponds to a 100% confidence that the nodule is an example of the first class.

In some embodiments, the at least one hardware processor is further programmed to: receive a longitudinal B-mode ultrasound image of the subject's thyroid; receive information indicating which portions of the longitudinal B-mode ultrasound correspond to the nodule; provide at least a portion of the longitudinal B-mode ultrasound image to the second trained classification model; and receive, from the second trained classification model, a second output indicative of a likelihood that the nodule is malignant.

In some embodiments, the at least one hardware processor is further programmed to: indicate that the nodule is benign in response to the output and the second output both indicating with 100% confidence that the nodule is benign.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 7 shows an example of a table of different resnet architectures that can be trained and used to automatically diagnose thyroid nodules in ultrasound image data in accordance with some embodiments of the disclosed subject matter.

FIG. 13 shows an example of various performance metrics based on outputs generated by systems for automatically diagnosing thyroid nodules implemented and trained in accordance with some embodiments of the disclosed subject matter.

DETAILED DESCRIPTION

Figure 1:
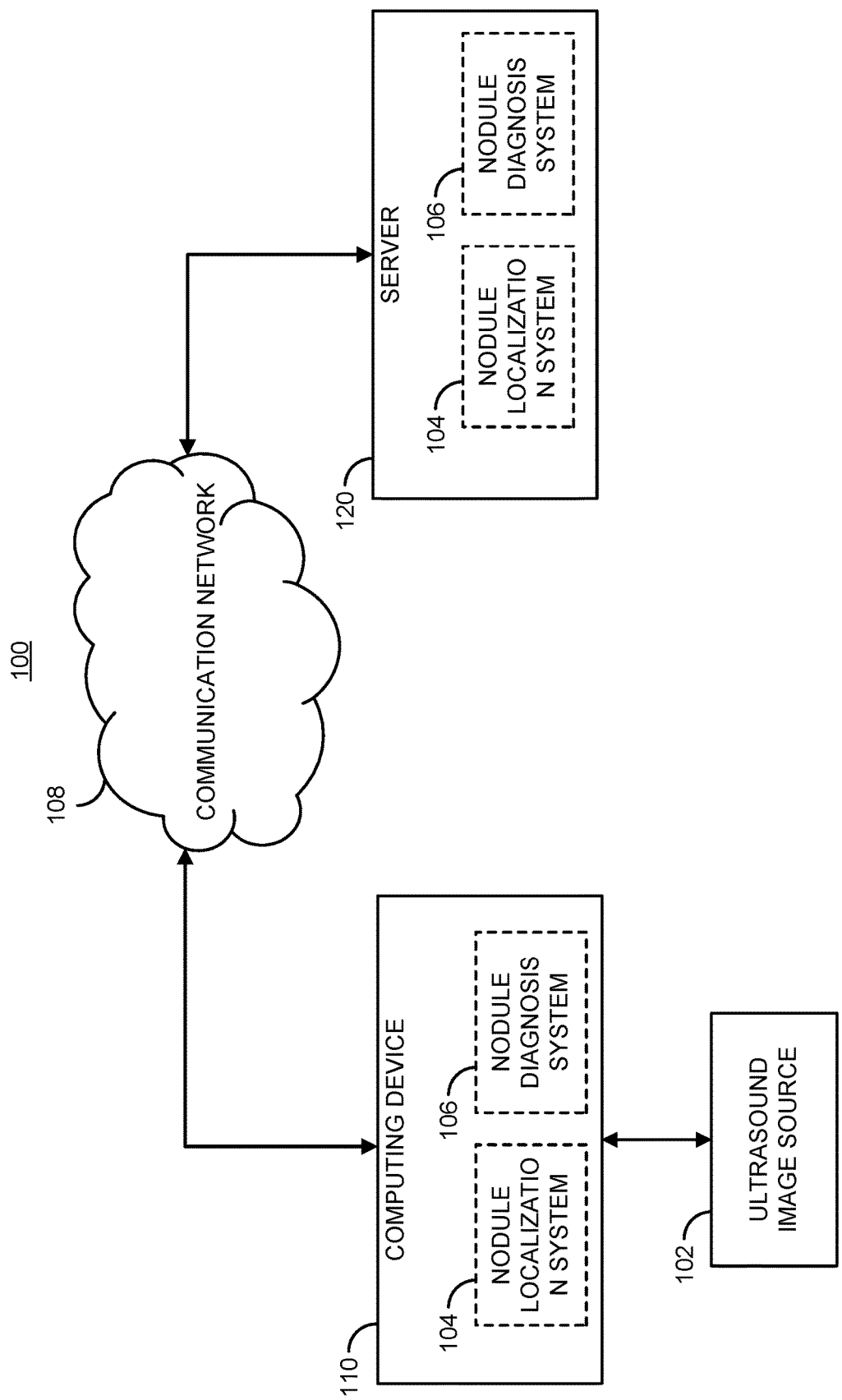
FIG. 1 shows an example of a system for automatically localizing and/or diagnosing thyroid nodules in accordance with some embodiments of the disclosed subject matter.

In accordance with various embodiments, mechanisms (which can, for example, include systems, methods, and media) for automatically diagnosing thyroid nodules are provided.

In general, ultrasound (US) is a safe and sensitive technique for the detection of thyroid nodules, and can be an important diagnostic tool in their assessment. For example, to evaluate and guide further investigation of thyroid nodules, imaging features such as size, echogenicity (e.g., hypoechoic or hyperechoic), composition (e.g., cystic, solid, or mixed), nodule margins, and the presence of calcification can be obtained from B-mode US techniques. The presence of internal blood flow, which is associated with malignancy, can be inferred from color Doppler US techniques. Additionally, tissue elasticity or stiffness properties can be obtained using shear wave elastography (SWE) US techniques, which have sometimes been used to assess thyroid nodules. Although several US features have been found to be associated with an increased risk of thyroid cancer, none of those features alone have both a high specificity and sensitivity for thyroid cancer.

Recent advances in machine learning techniques, and dramatic increases in computing power, have increased the ability of computers to recognize complex hierarchical patterns in images. These techniques can facilitate the discovery of patterns in medical images due to pathology and disease progression beyond what is recognizable by human eye. Modern machine learning techniques, such as deep learning, are capable of independently generating imaging features, and show promise in improving diagnostic accuracy of existing medical images.

In accordance with some embodiments of the disclosed subject matter, the mechanisms described herein can be used to train a first system (e.g., implemented using a first convolutional neural network (CNN)) to automatically segment nodules in 2D and/or 3D B-mode ultrasound images. For example, in some embodiments, labeled examples of two classes of B-mode image data (e.g., nodule and non-nodule) can be provided to a first CNN as training data.

In accordance with some embodiments of the disclosed subject matter, the mechanisms described herein can be used to train a second system (e.g., implemented using a second CNN) to automatically classify thyroid nodules as benign or malignant based on a combination of ultrasound images. For example, in some embodiments, labeled examples of two classes of B-mode, color Doppler, and SWE ultrasound image data (e.g., benign nodules and malignant nodules) can be provided to the second CNN as training data.

In some embodiments, the training data can be subdivided into three sets: a training set to be used during training of the CNN (e.g., using any suitable training technique, such as gradient descent), a verification set to be used during training of the CNN to determine performance after each training iteration, and a test set to be used after training is complete to determine performance of the trained CNN on novel examples of the classes.

FIG. 1 shows an example 100 of a system for automatically localizing and/or diagnosing thyroid nodules in accordance with some embodiments of the disclosed subject matter. As shown in FIG. 1, a computing device 110 can receive one or more types of ultrasound data from ultrasound image source 102. In some embodiments, computing device 110 can execute at least a portion of a nodule localization system 104 to automatically segment portions of thyroid ultrasound image data (e.g., 2D or 3D B-mode image data) received from ultrasound image source 102 that correspond to thyroid nodules. Additionally or alternatively, in some embodiments, computing device 110 can execute at least a portion of a nodule diagnosis system 106 to automatically classify nodules (e.g., segmented by nodule localization system 104) as benign or malignant based on thyroid ultrasound image data (e.g., a combination of 2D or 3D B-mode image data, color Doppler image data, and SWE image data) received from ultrasound image source 102.

Additionally or alternatively, in some embodiments, computing device 110 can communicate information about ultrasound data received from ultrasound image source 102 to a server 120 over a communication network 108, which can execute at least a portion of nodule localization system 104 to automatically segment nodules from thyroid ultrasound image data and/or at least a portion of nodule diagnosis system 106 to automatically diagnose a thyroid nodule as benign or malignant based on a thyroid nodule identified in ultrasound data. In such embodiments, server 120 can return information to computing device 110 (and/or any other suitable computing device) indicative of an output of nodule localization system 104 to automatically segment nodules form thyroid ultrasound image data and/or nodule diagnosis system 106, such as a segmented B-mode ultrasound image identifying one or more nodules, a diagnosis of a thyroid nodule as being benign or malignant, a report regarding the likelihood that the nodule is benign of malignant, etc. In some embodiments, computing device 110 and/or server 120 can be any suitable computing device or combination of devices, such as a desktop computer, a laptop computer, a smartphone, a tablet computer, a wearable computer, a server computer, a virtual machine being executed by a physical computing device, etc. As described below in connection with FIGS. 3-7, 10, and 11, nodule localization system 104 can use one or more trained CNNs to automatically segment thyroid nodules from thyroid ultrasound image data, and/or can provide information about one or more segmented thyroid nodule(s) to nodule diagnosis system 106. In some embodiments, nodule diagnosis system 106 can use one or more trained CNNs to automatically diagnose thyroid nodules by analyzing segmented thyroid ultrasound image data, and can present information about the determined diagnosis and/or segmented nodule(s) to a user (e.g., a physician).

In some embodiments, ultrasound image source 102 can be any suitable source of ultrasound image data, such as an ultrasound machine, another computing device (e.g., a server storing ultrasound image data), etc. In some embodiments, ultrasound image source 102 can be local to computing device 110. For example, ultrasound image source 102 can be incorporated with computing device 110 (e.g., computing device 110 can be configured as part of a device for capturing, scanning, and/or storing ultrasound images). As another example, ultrasound image source 102 can be connected to computing device 110 by a cable, a direct wireless link, etc. Additionally or alternatively, in some embodiments, ultrasound image source 102 can be located locally and/or remotely from computing device 110, and can communicate ultrasound image data to computing device 110 (and/or server 120) via a communication network (e.g., communication network 108).

In some embodiments, communication network 108 can be any suitable communication network or combination of communication networks. For example, communication network 108 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 2:
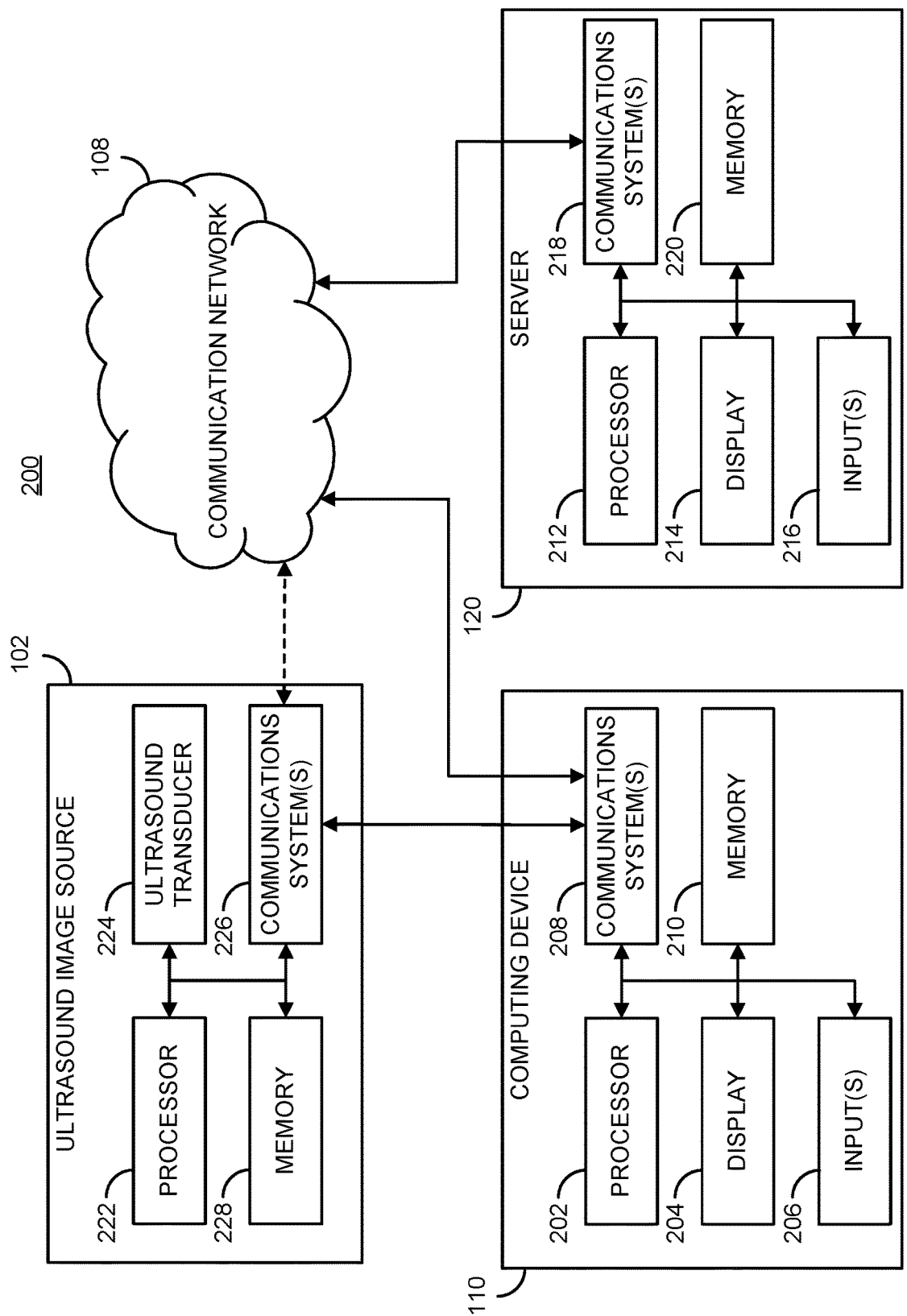
FIG. 2 shows an example of hardware that can be used to implement an ultrasound image source, a computing device, and a server in accordance with some embodiments of the disclosed subject matter.

FIG. 2 shows an example 200 of hardware that can be used to implement ultrasound image source 102, computing device 110, and server 120 in accordance with some embodiments of the disclosed subject matter. As shown in FIG. 2, in some embodiments, computing device 110 can include a processor 202, a display 204, one or more inputs 206, one or more communication systems 208, and/or memory 210. In some embodiments, processor 202 can be any suitable hardware processor or combination of processors, such as a central processing unit (CPU), a graphics processing unit (GPU), etc. In some embodiments, display 204 can include any suitable display devices, such as a computer monitor, a touchscreen, a television, etc. In some embodiments, inputs 206 can include any suitable input devices and/or sensors that can be used to receive user input, such as a keyboard, a mouse, a touchscreen, a microphone, etc.

In some embodiments, communications systems 208 can include any suitable hardware, firmware, and/or software for communicating information over communication network 108 and/or any other suitable communication networks. For example, communications systems 208 can include one or more transceivers, one or more communication chips and/or chip sets, etc. In a more particular example, communications systems 208 can include hardware, firmware and/or software that can be used to establish a Wi-Fi connection, a Bluetooth connection, a cellular connection, an Ethernet connection, etc.

In some embodiments, memory 210 can include any suitable storage device or devices that can be used to store instructions, values, etc., that can be used, for example, by processor 202 to present content using display 204, to communicate with server 120 via communications system(s) 208, etc. Memory 210 can include any suitable volatile memory, non-volatile memory, storage, or any suitable combination thereof. For example, memory 210 can include RAM, ROM, EEPROM, one or more flash drives, one or more hard disks, one or more solid state drives, one or more optical drives, etc. In some embodiments, memory 210 can have encoded thereon a computer program for controlling operation of computing device 110. In such embodiments, processor 202 can execute at least a portion of the computer program to present content (e.g., ultrasound images, user interfaces, graphics, tables, etc.), receive content from server 120, transmit information to server 120, etc.

In some embodiments, server 120 can include a processor 212, a display 214, one or more inputs 216, one or more communications systems 218, and/or memory 220. In some embodiments, processor 212 can be any suitable hardware processor or combination of processors, such as a CPU, a GPU, etc. In some embodiments, display 214 can include any suitable display devices, such as a computer monitor, a touchscreen, a television, etc. In some embodiments, inputs 216 can include any suitable input devices and/or sensors that can be used to receive user input, such as a keyboard, a mouse, a touchscreen, a microphone, etc.

In some embodiments, communications systems 218 can include any suitable hardware, firmware, and/or software for communicating information over communication network 108 and/or any other suitable communication networks. For example, communications systems 218 can include one or more transceivers, one or more communication chips and/or chip sets, etc. In a more particular example, communications systems 218 can include hardware, firmware and/or software that can be used to establish a Wi-Fi connection, a Bluetooth connection, a cellular connection, an Ethernet connection, etc.

In some embodiments, memory 220 can include any suitable storage device or devices that can be used to store instructions, values, etc., that can be used, for example, by processor 212 to present content using display 214, to communicate with one or more computing devices 110, etc. Memory 220 can include any suitable volatile memory, non-volatile memory, storage, or any suitable combination thereof. For example, memory 220 can include RAM, ROM, EEPROM, one or more flash drives, one or more hard disks, one or more solid state drives, one or more optical drives, etc. In some embodiments, memory 220 can have encoded thereon a server program for controlling operation of server 120. In such embodiments, processor 212 can execute at least a portion of the server program to transmit information and/or content (e.g., results of automatic thyroid nodule segmentation, results of automatic thyroid nodule diagnosis, a user interface, etc.) to one or more computing devices 110, receive information and/or content from one or more computing devices 110, receive instructions from one or more devices (e.g., a personal computer, a laptop computer, a tablet computer, a smartphone, etc.), etc.

In some embodiments, ultrasound image source 102 can include a processor 222, an ultrasound transducer 224, one or more communications systems 226, and/or memory 228. In some embodiments, processor 222 can be any suitable hardware processor or combination of processors, such as a CPU, a GPU, etc. In some embodiments, ultrasound transducer 224 can be any suitable ultrasound probe configured to generate US data corresponding to one or more US imaging modes (e.g., B-mode US, color Doppler US, SWE US, etc.). Additionally or alternatively, in some embodiments, ultrasound transducer 224 can include any suitable hardware, firmware, and/or software for coupling to and/or controlling operations of an ultrasound transducer. In some embodiments, one or more portions of ultrasound transducer 224 can be removable and/or replaceable (e.g., with a transducer that is configured to generate US data corresponding to a different mode, that is configured to generate US data with higher or lower resolution, etc.). Examples of ultrasound transducers that can be used to implement ultrasound transducer 224 can include a VL13-5 US transducer and/or an eL18-4 US probe (both available from PHILIPS). An example of an ultrasound machines that can be used to implement ultrasound image source 102 can include an EPIQ ultrasound machine (available from PHILIPS).

Note that, although not shown, ultrasound image source 102 can include any suitable inputs and/or outputs. For example, ultrasound image source 102 can include input devices and/or sensors that can be used to receive user input, such as a keyboard, a mouse, a touchscreen, a microphone, a trackpad, a trackball, etc. As another example, ultrasound image source 102 can include any suitable display devices, such as a computer monitor, a touchscreen, a television, etc., one or more speakers, etc.

In some embodiments, communications systems 226 can include any suitable hardware, firmware, and/or software for communicating information to computing device 110 (and, in some embodiments, over communication network 108 and/or any other suitable communication networks). For example, communications systems 226 can include one or more transceivers, one or more communication chips and/or chip sets, etc. In a more particular example, communications systems 226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 228 can include any suitable storage device or devices that can be used to store instructions, values, US image data, etc., that can be used, for example, by processor 222 to: control ultrasound transducer 224, and/or receive US data from ultrasound transducer 224; generate US images; present content (e.g., US images, a user interface, etc.) using a display; communicate with one or more computing devices 110; etc. Memory 228 can include any suitable volatile memory, non-volatile memory, storage, or any suitable combination thereof. For example, memory 228 can include RAM, ROM, EEPROM, one or more flash drives, one or more hard disks, one or more solid state drives, one or more optical drives, etc. In some embodiments, memory 228 can have encoded thereon a program for controlling operation of ultrasound image source 102. In such embodiments, processor 222 can execute at least a portion of the program to generate US images, transmit information and/or content (e.g., US image data) to one or more computing devices 110, receive information and/or content from one or more computing devices 110, receive instructions from one or more devices (e.g., a personal computer, a laptop computer, a tablet computer, a smartphone, etc.), etc.

Figure 3:
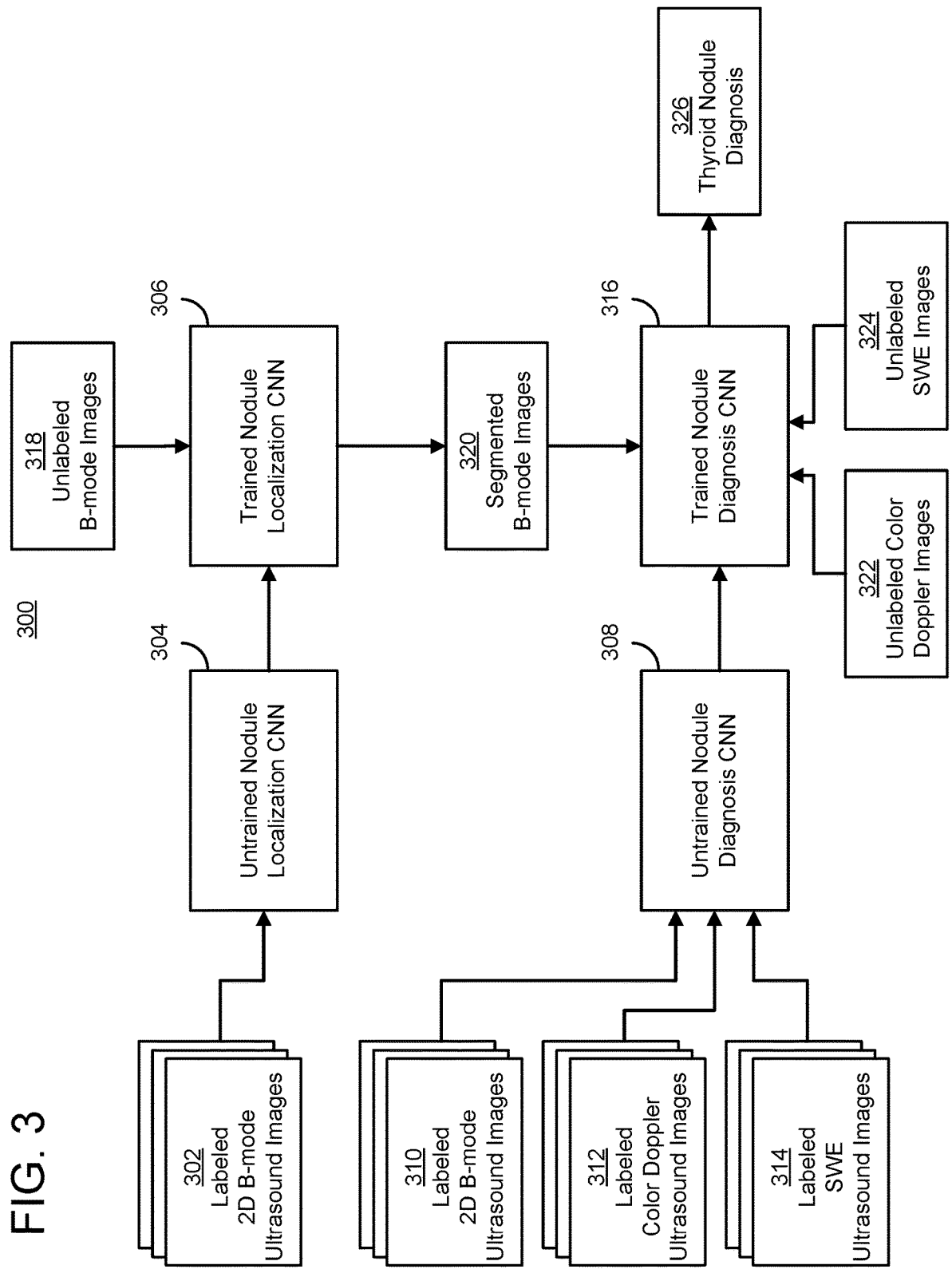
FIG. 3 shows an example of a flow for training and using mechanisms for automatically localizing and/or diagnosing thyroid nodules in accordance with some embodiments of the disclosed subject matter.

FIG. 3 shows an example 300 of a flow for training and using mechanisms for automatically localizing and diagnosing thyroid nodules in accordance with some embodiments of the disclosed subject matter. As shown in FIG. 3, labeled examples 302 of B-mode US images can be provided as training data to an untrained nodule localization CNN 304. For example, B-mode US images 302 can have areas that are labeled as corresponding to nodules, and areas that are labeled as not corresponding to nodules. In some embodiments, B-mode US images 302 can be labeled using any suitable technique or combination of techniques, such as labeling by one or more physicians that manually segment the nodules (if any) present in the B-mode US image. In some embodiments, B-mode US images 302 can be from any suitable source of B-mode US images. For example, B-mode US images 302 can be generated using one or more US machines that are used to capture US images of various subjects' thyroids. In such an example, B-mode US images 302 can be generated specifically for use as training data, and/or can be generated in the course of treatment for the subjects. In another example, B-mode US images 302 can be retrieved from the electronic medical records maintained by one or more medical providers. In some embodiments, B-mode US images 302 can be depict the subject's thyroid from any suitable probe orientation and/or position. For example, B-mode US images 302 can include transvers images and/or longitudinal images.

In some embodiments, a trained nodule localization CNN 306 can be created as the result of training untrained nodule localization CNN 304 using B-mode US images 302 as training data. In some embodiments, trained nodule localization CNN 306 can be trained using any suitable technique or combination of techniques. For example, techniques described below in connection with 404 of FIG. 4.

As shown in FIG. 3, labeled examples 310 of B-mode US images can be provided as training data to an untrained nodule diagnosis CNN 308. For example, B-mode US images 310 can have areas that are labeled as corresponding to nodules, and can be labeled as being an example of a benign nodule or a malignant nodule. In some embodiments, B-mode US images 310 can be labeled using any suitable technique or combination of techniques, such as labeling by one or more physicians that manually segment the nodules (if any) present in the B-mode US image, and assign a label to the nodule as benign or malignant based on the results of a biopsy (e.g., a fine needle aspiration biopsy). Additionally or alternatively, in some embodiments, B-mode US images 310 can be labeled automatically (e.g., by trained nodule localization CNN 306), and based on the results of a biopsy (e.g., manually, by extracting data from a report associated with the particular image to be used for training, etc.).

In some embodiments, B-mode US images 310 can be from any suitable source of B-mode US images. For example, B-mode US images 310 can be generated using one or more US machines that are used to capture US images of various subjects' thyroids, and for which a biopsy is performed to determine whether a particular nodule is benign or malignant. In such an example, B-mode US images 310 can be generated specifically for use as training data, and/or can be generated in the course of treatment for the subjects. In another example, B-mode US images 310 can be retrieved from one or more medical providers (e.g., from the medical providers electronic medical records) that have records indicating that a biopsy of a nodule was performed, and for which results of the biopsy are available.

In some embodiments, labeled examples 312 of color Doppler US images that each corresponds to at least a portion of a B-mode US image 310 can be provided as training data to an untrained nodule diagnosis CNN 308. For example, color Doppler US images 312 can have areas that are labeled as corresponding to nodules, and can be labeled as being an example of a benign nodule or a malignant nodule. In some embodiments, color Doppler US images 312 can be collected while collecting B-mode US image 310. In some embodiments, color Doppler US images 312 can be segmented manually (e.g., by a physician) or automatically (e.g., based on a corresponding B-mode US image 310). Alternatively, in some embodiments, nodule diagnosis CNN 308 can be trained using only B-mode US images 310 (e.g. without using color Doppler US images 312).

In some embodiments, labeled examples 314 of SWE US images that each corresponds to at least a portion of a B-mode US image 310 and a color Doppler US image 312 can be provided as training data to an untrained nodule diagnosis CNN 308. For example, SWE US images 314 can have areas that are labeled as corresponding to nodules, and can be labeled as being an example of a benign nodule or a malignant nodule. In some embodiments, SWE US images 314 can be collected while collecting B-mode US image 310. In some embodiments, SWE US images 314 can be segmented manually (e.g., by a physician) or automatically (e.g., based on a corresponding B-mode US image 310). Alternatively, in some embodiments, nodule diagnosis CNN 308 can be trained using only B-mode US images 310 (e.g. without using color Doppler US images 312 or SWE US images 314), using both B-mode US images 310 and color Doppler US images 312 (without using SWE US images 314), using both B-mode US images 310 and SWE US images 314 (e.g. without using color Doppler US images 312).

In some embodiments, a trained nodule diagnosis CNN 316 can be created as the result of training untrained nodule diagnosis CNN 308 using B-mode US images 310, color Doppler US images 312, and SWE US images 314 as training data. In some embodiments, trained nodule diagnosis CNN 316 can be trained using any suitable technique or combination of techniques. For example, techniques described below in connection with 504 of FIG. 5.

In some embodiments, an unlabeled B-mode US image 318 can be provided to trained nodule localization CNN 306, which can determine which portions of B-mode US image 318 correspond to a thyroid nodule, and which do not. In some embodiments, trained nodule localization CNN 306 can provide a segmented B-mode US image 320 to trained nodule diagnostic CNN 316. In some embodiments, trained nodule diagnostic CNN 316 can also receive an unlabeled color Doppler US image 322, and/or an unlabeled SWE US image 324 that correspond to the portion(s) of segmented B-mode US image 320 that are identified as nodules.

In some embodiments, using segmented B-mode US image 320, color Doppler US image 322, and/or an SWE US image 324, trained nodule diagnosis CNN 316 can generate a diagnosis 326 for at least one nodule included in segmented B-mode US image 320. For example, trained nodule diagnosis CNN 316 can provide one or more output values indicating whether the nodule is more likely to be benign or malignant, and the confidence with which the prediction was made.

Figure 4:
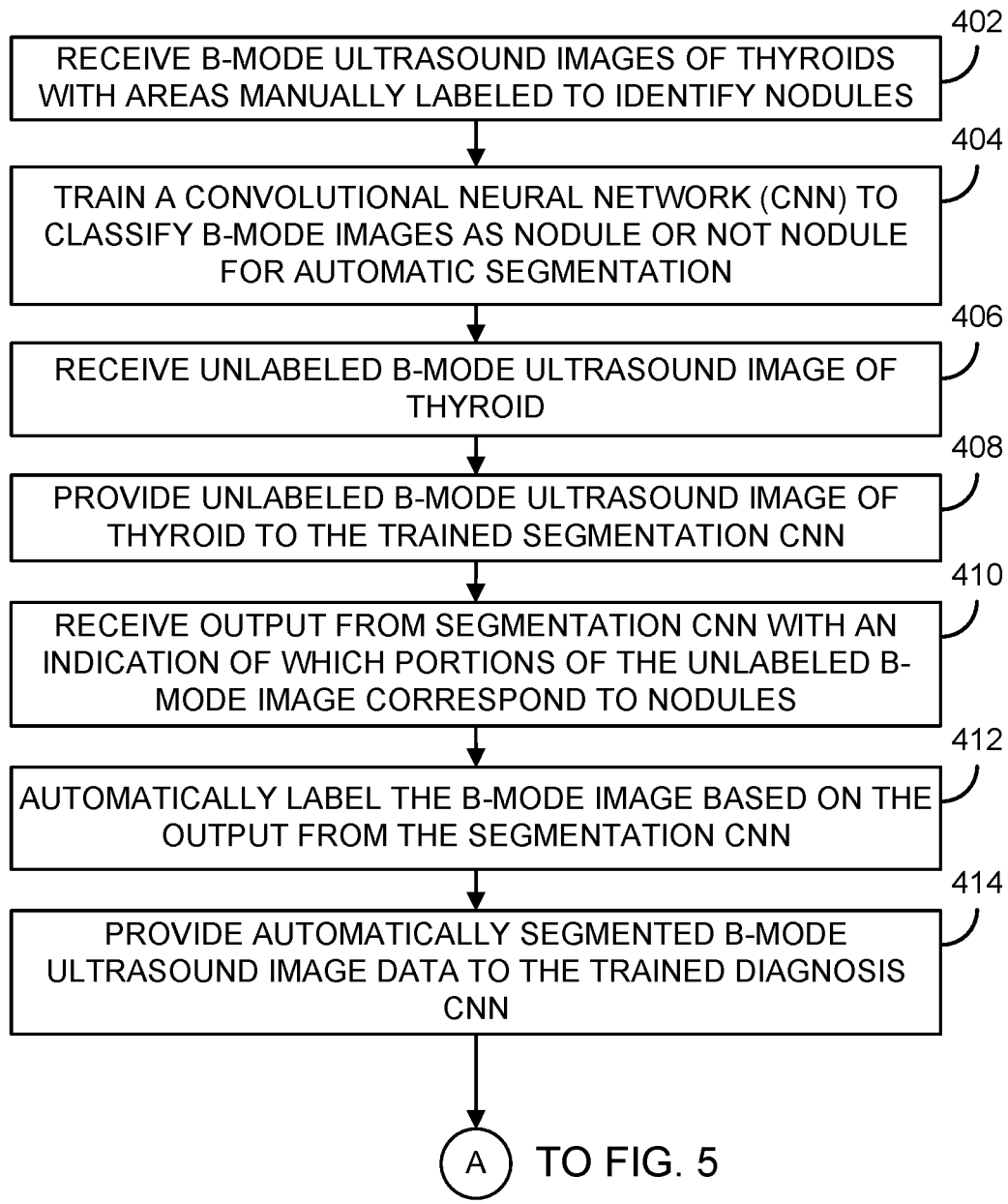
FIG. 4 shows an example of a process for training and using a system for automatically localizing thyroid nodules in accordance with some embodiments of the disclosed subject matter.

FIG. 4 shows an example 400 of a process for training and using a system for automatically localizing thyroid nodules in accordance with some embodiments of the disclosed subject matter. As shown in FIG. 4, process 400 can receive B-mode US images (e.g., labeled B-mode US images 304) with areas corresponding to nodules manually labeled and/or areas that do not include a nodule labeled. For example, a corpus of retrospective 2D thyroid B-mode US images (e.g., hundreds or thousands) that contain nodules can be collected, and labels and segmentations can be generated for the thyroid gland itself and/or nodules within the gland. In some embodiments, 3D volumes of the thyroid can be generated from free hand sweep using an electromagnetic (EM) tracker that is attached to a 2D US probe and records the orientation in which each 2D slice is acquired. Alternatively, 3D volumes can be generated using a mechanical 3D high frequency probe (e.g., a VL13-5 US transducer available from PHILIPS). As another example, US images can be captured using an EPIQ ultrasound scanner and eL18-4 probe (both available from PHILIPS) for localization and segmentation of nodules in 3D US.

At 404, process 400 can train a CNN to classify portions of B-mode US images as corresponding to a nodule or not corresponding to a nodule. In some embodiments, process 400 can train a CNN with any suitable architecture to classify portions of B-mode US images. For example, process 400 can train a CNN with a U-NET-based architecture to classify portions of B-mode US images as corresponding to a nodule or not corresponding to a nodule. An example of a U-NET architecture is described in Ronneberger et al., "U-Net: Convolutional Networks for Biomedical Image Segmentation," available at arxiv(dot)org/abs/1505.04597 (2015), which is hereby incorporated by reference herein in its entirety.

In some embodiments, process 400 can use any suitable technique or combination of techniques to train the CNN to classify portions of B-mode US images as nodule or non-nodule. For example, in some embodiments, process 400 can train the CNN from initialized (e.g., default) parameter values. Additionally or alternatively, in some embodiments, process 400 can use transfer learning techniques to further train a pre-trained CNN (e.g., a CNN with at least some parameters that have been determined through a training process).

In some embodiments, any suitable technique or combination of techniques can be used to train the nodule localization CNN. For example, process 400 can include subdividing the B-mode US images into a training set, a validation set, and a test set. Process 400 can include training the nodule localization CNN using the training set to augment the behavior of nodule localization CNN (e.g., by changing one or more parameters) to generate an iteration of nodule localization CNN. After each iteration, the validation set can be used to determine whether (and how much) performance of the CNN has improved compared to the previous iteration. After improvement slows or stops (e.g., after a particular number of iterations without an improvement above a threshold), process 400 can include using the test set to determine the performance of the trained nodule localization CNN. For example, this can be done to determine whether the trained CNN is overfitted to the validation set.

In some embodiments, images used during training of the CNN can be generated from 3D volumes that have been segmented to identify voxels that correspond to nodules. These 3D volumes can be resampled to generate many additional training, validation, and/or test images. For example, whereas the 3D volume was constructed based on US image data corresponding to certain planes, the 3D volume can be constructed to generate B-mode images along many additional planes that were not captured in the original data by sampling the voxels in the additional plane. In some embodiments, process 400 can use whole 2D B-mode US images as training data (e.g., rather than patches corresponding to just nodules) with each pixel labeled as corresponding to a nodule or not corresponding to a nodule (e.g., as a mask corresponding to the training image).

In some embodiments, process 400 can train the CNN to identify which pixels of an input 2D B-mode US image are likely to depict a portion of a nodule and which likely do not depict a portion of a nodule. In some such embodiments, the output of the CNN can indicate the likelihood that each pixel of the image is nodule or non-nodule, which can be used to generate a mask (e.g., for use by a nodule diagnosis CNN). Note that although the CNN trained at 404 is generally described as being trained using 2D B-mode US images to segment unlabeled 2D B-mode US images, this is merely an example, and process 400 can train a CNN using 3D B-mode US data to segment unlabeled 3D B-mode US data by labeling voxels as being nodule or non-nodule.

At 406, process 400 can receive an unlabeled B-mode US image that includes a portion of a subject's thyroid. For example, a US can be taken of the subject's thyroid, and an image from the US can be provided for segmentation by the trained nodule localization CNN.

At 408, process 400 can provide the unlabeled B-mode ultrasound to the trained nodule localization CNN for segmentation. In some embodiments, process 400 can provide an entire 2D B-mode US image to the trained nodule localization CNN for segmentation. Additionally or alternatively, if the data is received as 3D US data, process 400 can sample one or more 2D cross sections from the 3D US data (which may or may not each correspond to a slice used to construct the 3D US data), and can provide each cross section to the trained nodule localization CNN as input.

At 410, process 400 can receive output from the nodule localization CNN including an indication of which portion(s) of the B-mode US image are nodules. In some embodiments, the output of the nodule localization CNN can be a mask indicating which pixels of the input image (e.g., the input 2D B-mode US image) are likely to be nodule, and which are likely non-nodule. In some embodiments, the size of the output mask can be the same size as the input image (e.g., the output can be a matrix of values with an entry for each pixel in the input image).

At 412, process 400 can automatically label the B-mode US image based on the output of the trained nodule localization CNN. For example, process 400 can determine which pixels of the B-mode US image were classified as corresponding to a nodule with at least a threshold confidence (e.g., 50%, 75%, 90%, etc.). In some embodiments, a user can verify that nodules were labeled correctly by the trained nodule localization CNN prior to using the segmented image as input to a nodule diagnosis CNN. In some embodiments, the size of the mask can be increased to insure that tissue adjacent to the nodule is used during training of the nodule diagnosis CNN.

At 414, process 400 can provide an automatically segmented B-mode US image to a trained nodule diagnosis CNN. For example, process 400 can provide the B-mode US image, the location represented in the image (e.g., angle to one or more planes of the body), and/or information about which portions correspond to a nodule (e.g., as a mask associated with the B-mode US image). In some embodiments, process 400 can provide the B-mode image and/or a mask representing the nodule to the trained nodule diagnosis CNN.

Figure 5:
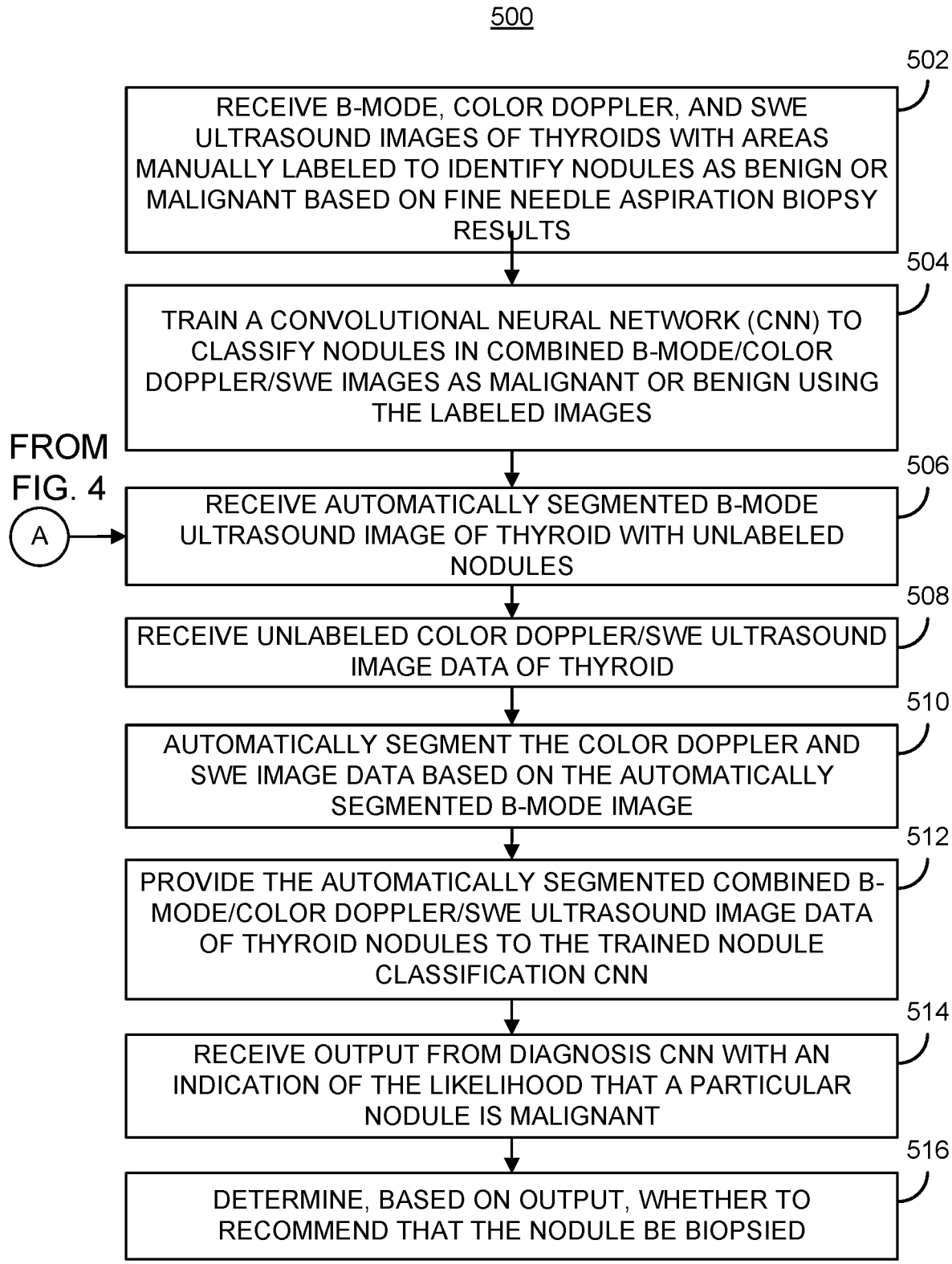
FIG. 5 shows an example of a process for training and using a system for automatically diagnosing thyroid nodules in accordance with some embodiments of the disclosed subject matter.

FIG. 5 shows an example 500 of a process for training and using a system for automatically diagnosing thyroid nodules in accordance with some embodiments of the disclosed subject matter. As shown in FIG. 5, at 502, process 500 can receive B-mode, color Doppler, and/or SWE US images with areas manually labeled to identify nodules in the images, and to identify whether the nodule was found to be benign or malignant (e.g., based on a fine needle aspiration biopsy).

In some embodiments, combined B-mode, color Doppler, and/or SWE US images can be collected from subject's (e.g., dozens, hundreds, etc.) that have received, or will receive, a fine needle aspiration biopsy. In some embodiments, the data can be collected using an EPIQ ultrasound scanner with an eL18-4 probe (both available from PHILIPS) that can be configured to acquire B-mode, color Doppler, and SWE images. In some embodiments, EM tracking can be used to create freehand sweep 3D US data.

At 504, process 500 can train a CNN to classify nodules in the B-mode, color Doppler, and/or SWE US images as benign or malignant. In some embodiments, process 500 can train a CNN with any suitable architecture to classify nodules included in US data as being benign or malignant. For example, process 500 can train a CNN with a resnet-based architecture to classify nodules represented in US data as being malignant or benign. In a more particular example, process 500 can train a CNN with a resnet-50 architecture. Examples of resnet-based architectures are described in He et al., "Deep Residual Learning for Image Recognition," available at arxiv(dot)org/abs/1512.03385 (2015), which is hereby incorporated by reference herein in its entirety. As another example, an inception-based architecture to classify nodules represented in US data as being malignant or benign. In a more particular example, process 500 can train a CNN with an inception V3 architecture. Examples of inception-based architectures are described in Szegedy, et al. "Rethinking the Inception Architecture for Computer Vision," (2016), which is hereby incorporated by reference herein in its entirety.

In some embodiments, process 500 can use any suitable technique or combination of techniques to train the CNN to classify portions US data corresponding to nodules as benign or malignant. For example, in some embodiments, process 500 can train the CNN from initialized (e.g., default) parameter values. Additionally or alternatively, in some embodiments, process 500 can use transfer learning techniques to further train a pre-trained CNN (e.g., a CNN with at least some parameters that have been determined through a training process). For example, the CNN can be trained as a general purpose image classifier that is trained to determine whether particular classes of object are present in an image.

In some embodiments, any suitable technique or combination of techniques can be used to train the nodule diagnosis CNN. For example, process 500 can include subdividing the combined US images into a training set, a validation set, and a test set. Process 500 can include training the nodule diagnosis CNN using the training set to augment the behavior of the nodule diagnosis CNN (e.g., by changing one or more parameters) to generate an iteration of nodule diagnosis CNN. After each iteration, the validation set can be used to determine whether (and how much) performance of the CNN has improved compared to the previous iteration. After improvement slows or stops (e.g., after a particular number of iterations without an improvement above a threshold), process 500 can include using the test set to determine the performance of the trained nodule localization CNN. For example, this can be done to determine whether the trained CNN is overfitted to the validation set.

At 506, process 500 can receive a segmented B-mode US image(s) of a thyroid with unlabeled nodules (i.e., not labeled as benign or malignant). In some embodiments, the segmented B-mode US image can be an image that was automatically segments (e.g., by trained nodule localization CNN 306). Additionally or alternatively, in some embodiments, the segmented B-mode US image can be an image that was segmented manually (e.g., by a physician) and/or under the direction of a human operator (e.g., a physician can confirm that the segmenting is accurate or adjust the segmenting that was automatically performed). In some embodiments, the segmentation and the B-mode US image can be received separately or as combined information. For example, the B-mode US image can be received in connection with a mask with pixels labeled as nodule or non-nodule. As another example, the B-mode US image can be modified to indicate which portion of corresponds to a nodule. In a more particular example, information can be added to an additional channel (e.g., if the B-mode US image uses only a brightness channel, mask information can be added as a second channel). In another more particular example, pixels of the B-mode US image that do not correspond to the nodule can be set to a particular value (e.g., black or white corresponding to brightness values of 0 or 255 in an 8-bit grayscale image).

At 508, process 500 can receive unlabeled color Doppler and SWE US images corresponding to the automatically segmented B-mode US image at 506. In some embodiments, 508 can be omitted and/or one of the types of images can be omitted. For example, in some embodiments, classification of the nodule can be based on only the B-mode US image. As another example, classification of the nodule can be based on the B-mode US image and either a color Doppler image or a SWE US image.

At 510, process 500 can automatically segment the unlabeled color Doppler and SWE US images based on the automatically segmented B-mode US image. For example, in some embodiments, labels from the B-mode US image can be used to label the color Doppler and SWE US images. As another example, labels from the B-mode US image can be used to select portions of the B-mode, color Doppler, and SWE US images to be provided to the nodule diagnosis CNN. As yet another example, the B-mode, color Doppler, and SWE US images can be provided to the nodule diagnosis CNN as data on three different channels, and the labels from the B-mode US image can be used as a proxies for which portions of the color Doppler and SWE US images. As still another example, the B-mode, color Doppler, and SWE US images can be provided to the nodule diagnosis CNN as data on up to three different channels, and a mask indicating which portions of the B-mode US image (and, in some cases, the color Doppler and/or SWE images) correspond to nodule can be provided on a different channel (e.g., a second, third or fourth channel). As a further example, separate nodule diagnosis CNNs can be trained for different modes (e.g., a nodule diagnosis CNN trained using B-mode US images, a second nodule diagnosis CNN trained using color Doppler US images, and/or a third nodule diagnosis CNN trained using SWE US images), and the output of each CNN can be combined (e.g., by concatenating the results, averaging the results, polling the results to determine how many of the CNNs predicted the same outcome, etc.). In such an example, the images from different modes can be generated simultaneously or separately, and nodule regions do not necessarily appear in the same region of each image and/or the images need not necessarily be generated from images captured from the same location and/or orientation. In such an example, an appropriate nodule mask (e.g., generated manually, automatically, or semi-automatically) for each image mode indicating which portion(s) of the image corresponds to nodule can be provided on a second channel of any or all of CNNs.

At 512, process 500 can provide at least a portion of the segmented combined B-mode, color Doppler, and/or SWE US images that correspond to a particular nodule to be classified to the trained nodule diagnosis CNN. For example, output of the trained nodule localization CNN can be used to extract an image corresponding to a particular nodule (with some surrounding tissue also represented) from each of the B-mode US image data, the color Doppler US image data, and/or the SWE US image data. In some embodiments, image data from multiple modes can be provided as input simultaneously. For example, each mode can be provided as input to a different channel of the trained nodule diagnosis CNN (e.g., similar to red, green, and blue channels that are sometimes used in CNNs for classifying color images). Alternatively, in some embodiments, image data corresponding to each mode can be provided as input to the trained nodule diagnosis CNN sequentially. In some embodiments, the B-mode US image provided as input can be a portion of a B-mode US image that was provided as input to the trained nodule localization CNN. In some embodiments, a mask with values indicative of which portion(s) of the B-mode, color Doppler, and SWE US images correspond to nodule and/or which do not correspond to nodule can be provided to the trained nodule diagnosis CNN (e.g., on a separate channel).

At 514, process 500 can receive output from the trained nodule diagnosis CNN with an indication of the likelihood that the nodule being classified is benign or malignant. In some embodiments, the output received at 514 can include confidence values associated with a benign class and/or a malignant class.

At 516, process 500 can determine, based on the output, whether the nodule is relatively likely to be malignant, or benign. In some embodiments, based on the output, process 500 can provide a recommendation of whether the nodule should be biopsied. In some embodiments, process 500 can receive information that can be used to generate a class activation map and/or gradient backpropagation information that can be used to identify which portion of a nodule was most important to the prediction generated by the trained nodule diagnosis CNN.

In some embodiments, process 500 can recommend that no biopsy be performed when the output of the trained nodule diagnosis CNN indicates that the nodule is benign at 100% confidence. Otherwise, in some embodiments, process 500 can output an indication of the likelihood that the nodule is benign and/or malignant, and a physician can determine whether a biopsy should be performed.

Figure 6:
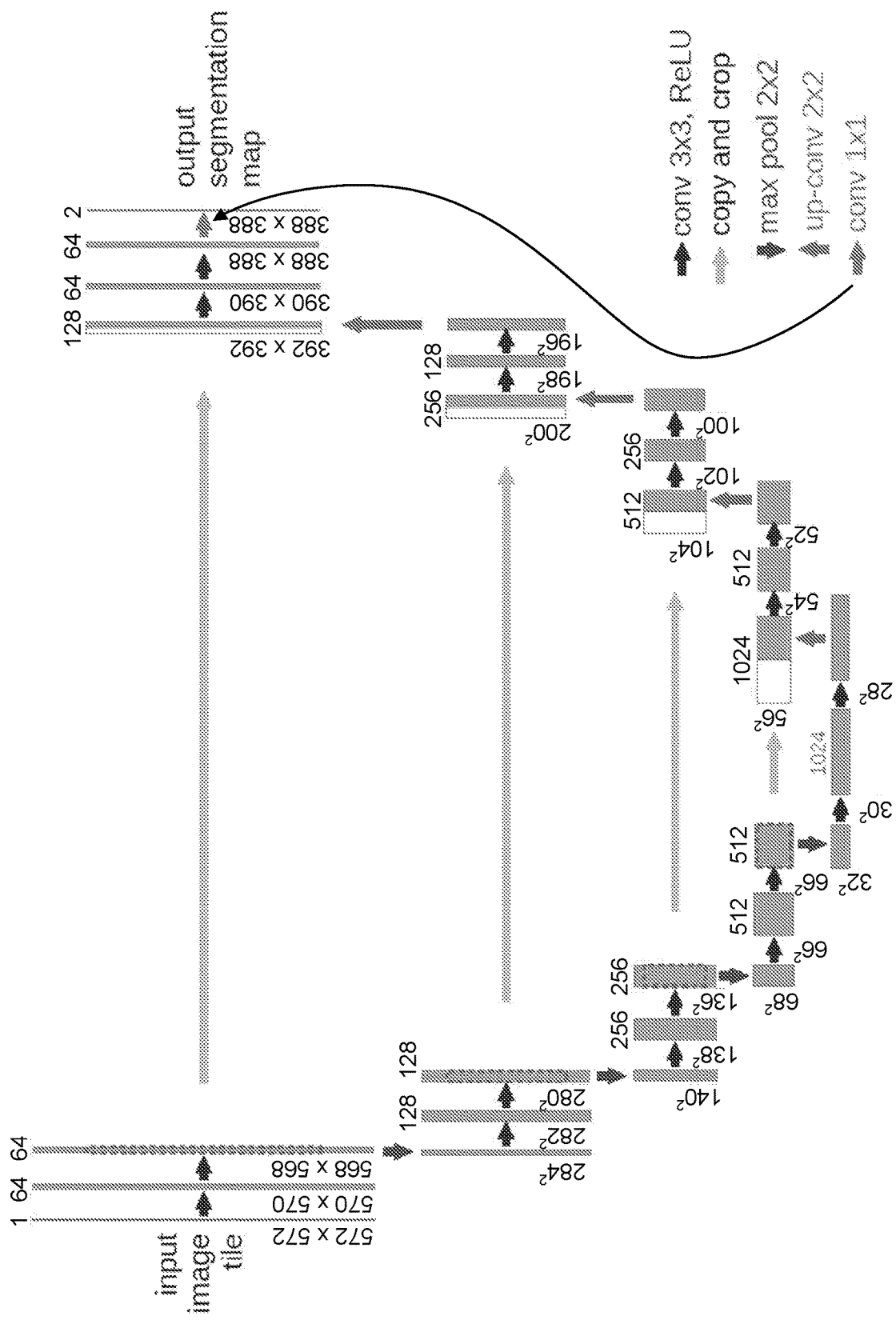
FIG. 6 shows an example of a U-Net-based CNN topology that can be trained and used to automatically segment thyroid nodules in ultrasound image data in accordance with some embodiments of the disclosed subject matter.

FIG. 6 shows an example of a U-Net-based CNN topology that is described in Ronneberger et al., "U-Net: Convolutional Networks for Biomedical Image Segmentation" that can be trained and used to automatically segment thyroid nodules in ultrasound image data in accordance with some embodiments of the disclosed subject matter. As described above in connection with FIG. 4, a CNN based on the topology shown in FIG. 6 can be trained from scratch to classify pixels of a B-mode US image as corresponding to nodule or non-nodule. For example, as shown in FIG. 6, the B-mode US image can be converted to a 572×572 pixel image. As another example, the B-mode US image can be converted to 256×256 pixels, 512×512 pixels, etc.

FIG. 7 shows an example of a table of various resnet architectures that can be trained as image classification CNNs that are described in He et al., "Deep Residual Learning for Image Recognition," that can be trained and used to automatically diagnose thyroid nodules in ultrasound image data in accordance with some embodiments of the disclosed subject matter. As described above in connection with FIG. 5, a CNN based on the 50 layer architecture described in the table of FIG. 7 can be trained from scratch to classify multimode US images of a nodule as being benign or likely malignant, which can be used to assist a physician determine whether to perform a biopsy of the nodule. Alternatively, in some embodiments, the 50 layer architecture described in the table of FIG. 7 can be trained from initialized (e.g., default) parameter values and/or using transfer learning techniques to further train a pre-trained CNN (e.g., a CNN with at least some parameters that have been determined through a training process).

Figure 8:
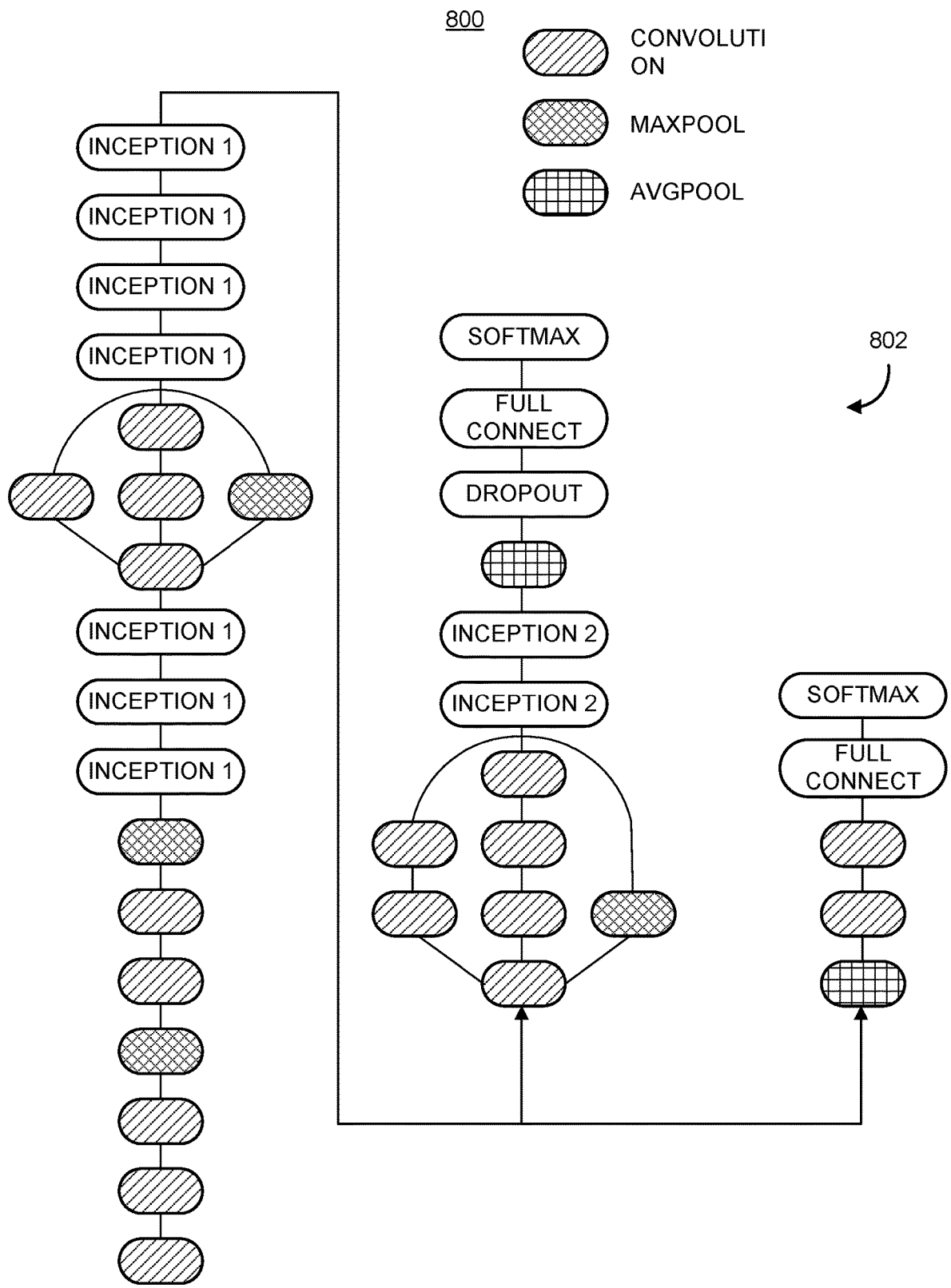
FIG. 8 shows an example of a topology of a CNN that can be trained and used to automatically segment or automatically diagnose thyroid nodules in ultrasound image data in accordance with some embodiments of the disclosed subject matter.

FIG. 8 shows an example 800 of a topology of a CNN 802 that can be trained and used to automatically segment and/or automatically diagnose thyroid nodules in ultrasound image data in accordance with some embodiments of the disclosed subject matter. Note that although the mechanisms described herein are described as being implemented using a U-NET-based CNN and a resnet-based CNN to localize and diagnose nodules, respectively, these are examples, and other CNN topologies and/or techniques for training can be adapted for use with the techniques described herein. For example, in some embodiments, CNN 802 can have a similar topology to a CNN described in Szegedy, et al. "Rethinking the Inception Architecture for Computer Vision."

Figure 9:
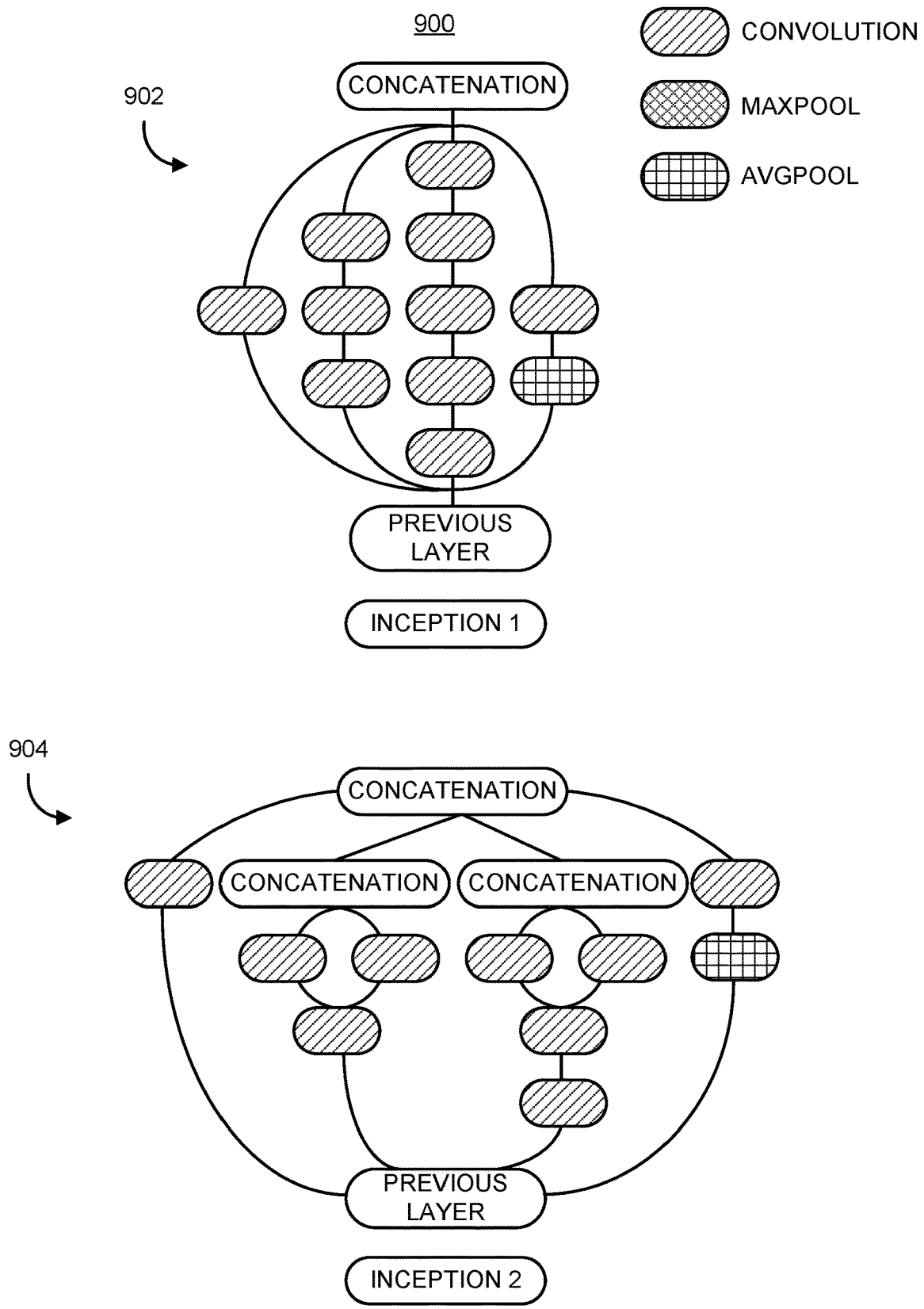
FIG. 9 shows an example of inception modules that can be used in the CNN topology of FIG. 8 in accordance with some embodiments of the disclosed subject matter.

FIG. 9 shows an example 900 of inception modules 902 and 904 used in CNN 802 in accordance with some embodiments of the disclosed subject matter. In some embodiments, inception modules 902 and 904 can have similar topologies to inception modules described in Szegedy, et al. "Rethinking the Inception Architecture for Computer Vision."

An example system for classifying images of nodules in multimode US data implemented in accordance with some embodiments of the disclosed subject in which segmented B-mode, color Doppler, and SWE US images were used to automatically predict benign or malignant class membership of a thyroid nodule achieved 100% sensitivity (i.e., all malignant tumors were classified as being malignant, there were zero false negatives), and 45% specificity (i.e., 45% of benign nodules were properly classified as negative, while 55% of benign nodules were improperly classified as positive) on a test dataset of 24 nodules that included 19 benign nodules and 5 malignant nodules. Based on these results, a system implemented in accordance with some embodiments of the disclosed subject matter can indicate when a biopsy is not needed about half the time, while being unlikely to indicate that a biopsy is unnecessary when a nodule is actually malignant. As described above, conventional techniques err on the side of performing biopsies, but only 9.2-13.0% of biopsies result in a diagnosis of a malignant nodule. That is, the false positive rate is relatively high, as around 90% of nodules that are biopsied via FNA are benign, which suggests a much higher than 55% false positive rate that was achieved with an automated nodule diagnosis system implemented in accordance with some embodiments of the disclosed subject matter.

Figure 10:
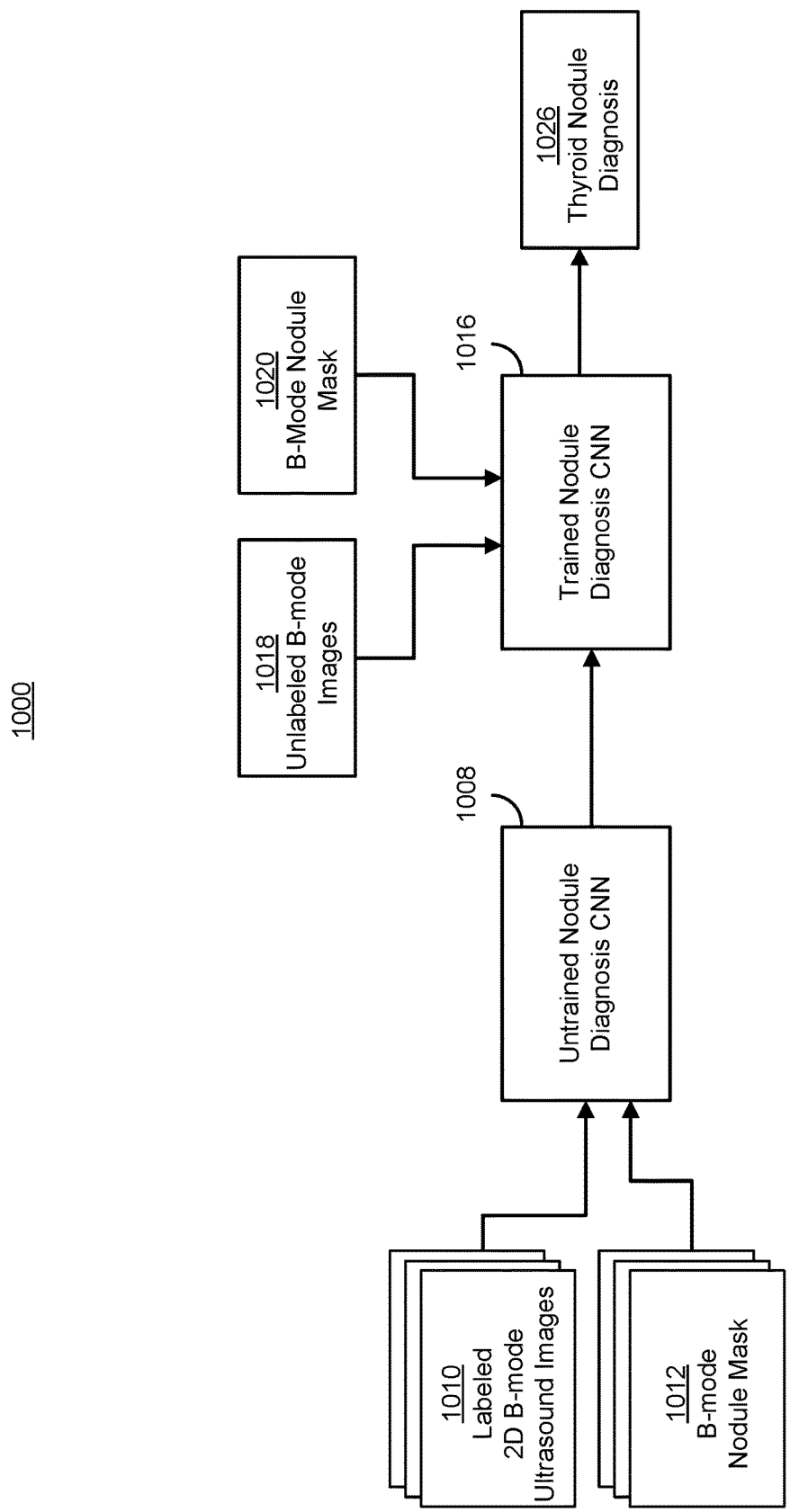
FIG. 10 shows an example of a flow for training and using mechanisms for automatically diagnosing thyroid nodules in accordance with some embodiments of the disclosed subject matter.

FIG. 10 shows an example 1000 of a flow for training and using mechanisms for automatically diagnosing thyroid nodules in accordance with some embodiments of the disclosed subject matter. As shown in FIG. 10, As shown in FIG. 10, labeled examples 1010 of B-mode US images can be provided as training data to an untrained nodule diagnosis CNN 1008. For example, B-mode US images 1010 can depict one or more nodules, and can be labeled as being an example of a benign nodule or a malignant nodule. In some embodiments, B-mode US images 1010 can be labeled using any suitable technique or combination of techniques, such as labeling by one or more physicians that manually segment the nodules (if any) present in the B-mode US image, and assign a label to the nodule as benign or malignant based on the results of a biopsy (e.g., a fine needle aspiration biopsy).

In some embodiments, B-mode US images 1010 can be from any suitable source of B-mode US images. For example, B-mode US images 1010 can be generated using one or more US machines that are used to capture US images of various subjects' thyroids, and for which a biopsy is performed to determine whether a particular nodule is benign or malignant. In such an example, B-mode US images 1010 can be generated specifically for use as training data, and/or can be generated in the course of treatment for the subjects and collected retrospectively. In another example, B-mode US images 1010 can be retrieved from one or more medical providers (e.g., from the medical providers electronic medical records) that have records indicating that a biopsy of a nodule was performed, and for which results of the biopsy are available.

In some embodiments, each B-mode US image 1010 can be associated with information indicating which portion(s) of the image data corresponds to a thyroid nodule. For example, each B-mode US image 1010 can be associated with a mask 1012 formatted as an array of pixels that each correspond to one or more co-located pixels of the corresponding B-mode US image 1010. In such an example, each pixel in the mask can be assigned a value of 0 indicating that the pixel does not correspond to a nodule, or a value of 1 indicating that the pixel does correspond to a nodule (and/or tissue adjacent to the nodule). As another example, each B-mode US image 1010 can be formatted with multiple channels in which a first channel correspond to the US data and a second channel is used to indicate which pixels of the image correspond to a nodule. In some embodiments, each B-mode US image 1010 can be scaled such that each pixel has a value between zero and one. For example, each brightness value can be divided by the maximum brightness. In a more particular example, an US image that uses a byte (i.e., 8 bits) to represent the brightness at each pixel such that each pixel can be assigned a brightness values from 0 to 255, and accordingly each pixel value can be divided by 255 to ensure that the value of pixel has a value from 0 to 1.

In some embodiments, mask 1012 (or other data used to indicate which portion(s) of B-mode US image 1010 corresponds to a nodule(s)) can be generated using any suitable technique or combination of techniques. For example, mask 1012 can be generated based on a manual segmentation of the B-mode US image 1010. In such an example, a physician (or other competent user) can identify which portion(s) of a particular B-mode US image 1010 corresponds to a nodule (e.g., using a computing device to draw a line around the area or highlight the area of the nodule, by drawing a line around the nodule or highlighting the nodule on a printout of the US image). In such an example, mask 1012 for that US image can be generated based on the segmentation by the user.

As another example, mask 1012 can be generated automatically. In a more particular example, mask 1012 can be generated based on an output of a trained nodule localization model (e.g., trained nodule localization CNN 306).

In some embodiments, a trained nodule diagnosis CNN 1016 can be created as the result of training untrained nodule diagnosis CNN 1008 using B-mode US images 1010 and corresponding masks 1012. In some embodiments, trained nodule diagnosis CNN 1016 can be trained using any suitable technique or combination of techniques. For example, techniques described below in connection with 1104 of FIG. 11.

In some embodiments, an unlabeled B-mode US image 1018 can be provided to trained nodule diagnostic CNN 1016. In some embodiments, trained nodule diagnostic CNN 1016 can also receive a correspond mask 1020 indicating which portion(s) of B-mode US image 1018 corresponds to a thyroid nodule.

In some embodiments, using B-mode US image 1018 and mask 1020, trained nodule diagnosis CNN 1016 can generate a diagnosis 1026 for at least one nodule included in B-mode US image 1018. For example, trained nodule diagnosis CNN 1016 can provide one or more output values indicating whether the nodule is more likely to be benign or malignant, and the confidence with which the prediction was made.

Figure 11:
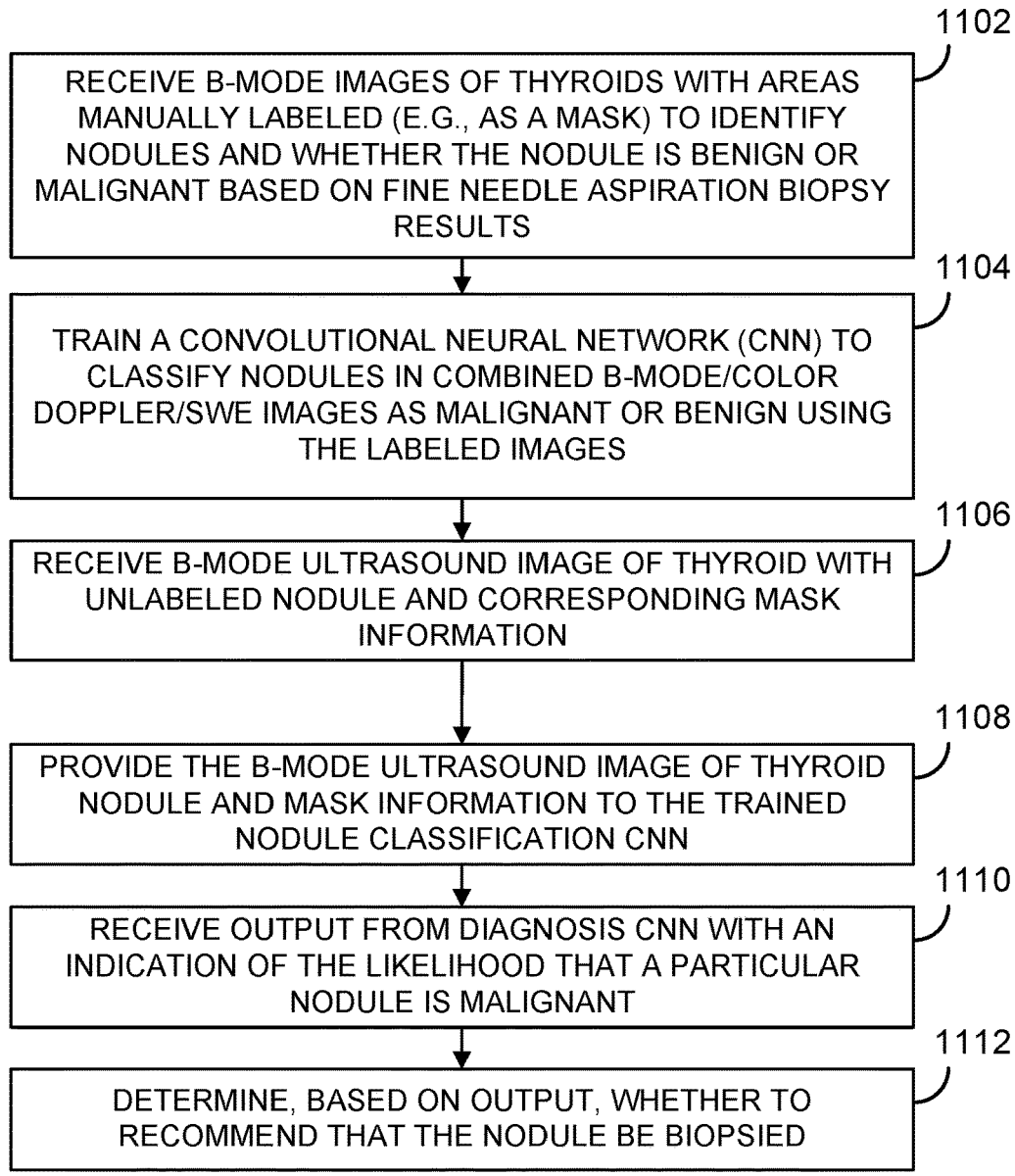
FIG. 11 shows an example of another process for training and using a system for automatically diagnosing thyroid nodules in accordance with some embodiments of the disclosed subject matter.

FIG. 11 shows an example 1100 of a process for training and using a system for automatically diagnosing thyroid nodules in accordance with some embodiments of the disclosed subject matter. As shown in FIG. 11, at 1102, process 1100 can receive B-mode US images with areas manually labeled to identify nodules in the images (e.g., as a mask), and information indicating whether the nodule was benign or malignant (e.g., based on a fine needle aspiration biopsy).

In some embodiments, B-mode US images can be collected from subject's (e.g., dozens, hundreds, etc.) that have received, or will receive, a fine needle aspiration biopsy. In some embodiments, the data can be collected using an EPIQ ultrasound scanner with an eL18-4 probe (both available from PHILIPS) that can be configured to acquire B-mode, color Doppler, and SWE images. In some embodiments, EM tracking can be used to create freehand sweep 3D US data.

At 1104, process 1100 can train a CNN to classify nodules in the B-mode US images as benign or malignant. In some embodiments, process 1100 can train a CNN with any suitable architecture to classify nodules included in US data as being benign or malignant. For example, process 1100 can train a CNN with a resnet-based architecture to classify nodules represented in US data as being malignant or benign. In a more particular example, process 1100 can train a CNN with a resnet-50 architecture. As another example, an inception-based architecture to classify nodules represented in US data as being malignant or benign. In a more particular example, process 1100 can train a CNN with an architecture based on inception V3.

In some embodiments, process 1100 can use any suitable technique or combination of techniques to train the CNN to classify portions US data corresponding to nodules as benign or malignant. For example, in some embodiments, process 1000 can train the CNN from initialized (e.g., default) parameter values. Additionally or alternatively, in some embodiments, process 1000 can use transfer learning techniques to further train a pre-trained CNN (e.g., a CNN with at least some parameters that have been determined through a training process). For example, the CNN can be trained as a general purpose image classifier that is trained to determine whether particular classes of object are present in an image.

In some embodiments, any suitable technique or combination of techniques can be used to train the nodule diagnosis CNN. For example, process 1100 can include subdividing the combined US images into a training set, a validation set, and a test set. Process 1100 can include training the nodule diagnosis CNN using the training set to augment the behavior of the nodule diagnosis CNN (e.g., by changing one or more parameters) to generate an iteration of nodule diagnosis CNN. After each iteration, the validation set can be used to determine whether (and how much) performance of the CNN has improved compared to the previous iteration. After improvement slows or stops (e.g., after a particular number of iterations without an improvement above a threshold), process 1100 can include using the test set to determine the performance of the trained nodule localization CNN. For example, this can be done to determine whether the trained CNN is overfitted to the validation set.

At 1106, process 1100 can receive a B-mode US image(s) of a thyroid with an unlabeled nodule(s) (i.e., not labeled as benign or malignant) and mask information indicating a portion of the B-mode US image corresponding to the nodule(s). In some embodiments, the mask information can be information that was automatically generated (e.g., by trained nodule localization CNN 306). Additionally or alternatively, in some embodiments, the mask information can be based on a B-mode US image that was segmented manually (e.g., by a physician) and/or under the direction of a human operator (e.g., a physician can confirm that the segmenting is accurate or adjust the segmenting that was automatically performed). In some embodiments, the B-mode US image and mask information can be received separately or as combined information. For example, the B-mode US image can be received in connection with a mask with pixels labeled as nodule or non-nodule. As another example, the B-mode US image can be modified to indicate which portion of corresponds to a nodule. In a more particular example, information can be added to an additional channel of the B-mode US image (e.g., if the B-mode US image uses only a brightness channel, mask information can be added as a second channel). In another more particular example, pixels of the B-mode US image that do not correspond to the nodule can be set to a particular value (e.g., black or white corresponding to brightness values of 0 or 255 in an 8-bit grayscale image). In yet another more particular example, the B-mode US image can be modified to exclude portions that do not correspond to a nodule (e.g., the image can be cropped to exclude portions that do not correspond to a nodule).

At 1108, process 1100 can provide at least a portion of the B-mode US image that corresponds to a particular nodule and corresponding mask information to be classified to the trained nodule diagnosis CNN. In some embodiments, process 1100 can receive a transverse B-mode US image and/or a longitudinal transvers B-mode US image at 1108.

At 1110, process 1100 can receive output from the trained nodule diagnosis CNN with an indication of the likelihood that the nodule being classified is benign or malignant. In some embodiments, the output received at 1110 can include confidence values associated with a benign class and/or a malignant class.

At 1112, process 1100 can determine, based on the output, whether the nodule is relatively likely to be malignant, or benign. In some embodiments, based on the output, process 1100 can provide a recommendation of whether the nodule should be biopsied. In some embodiments, process 1100 can receive information that can be used to generate a class activation map and/or gradient backpropagation information that can be used to identify which portion of a nodule was most important to the prediction generated by the trained nodule diagnosis CNN (e.g., as shown in FIG. 13).

In some embodiments, process 1100 can recommend that no biopsy be performed when the output of the trained nodule diagnosis CNN indicates that the nodule is benign at 100% confidence. Otherwise, in some embodiments, process 1100 can output an indication of the likelihood that the nodule is benign and/or malignant, and a physician can determine whether a biopsy should be performed. In some embodiments, both a transverse and longitudinal B-mode US image of the nodule can be provided (e.g., sequentially) to the trained nodule diagnosis CNN, and if the CNN indicates that either is likely to be malignant (e.g., not 100% likely to be benign), the CNN can indicate (or the physician can determine) that the nodule should be biopsied.

Figure 12A:
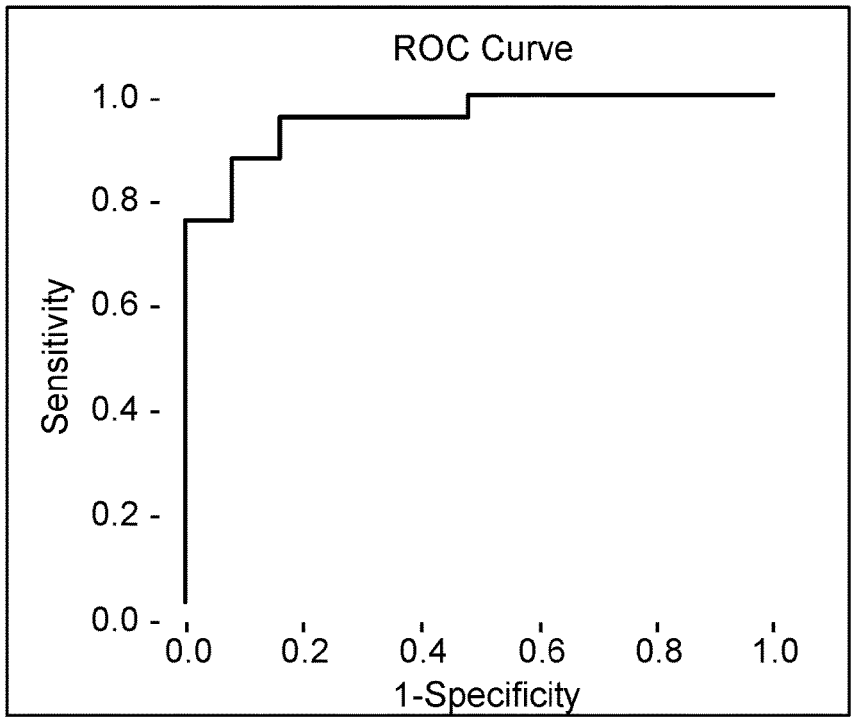
FIG. 12A shows a Receiver Operating Characteristic (ROC) curve illustrating the performance, using transverse ultrasound images, of a system for automatically diagnosing thyroid nodules implemented and trained in accordance with some embodiments of the disclosed subject matter.
Figure 12B:
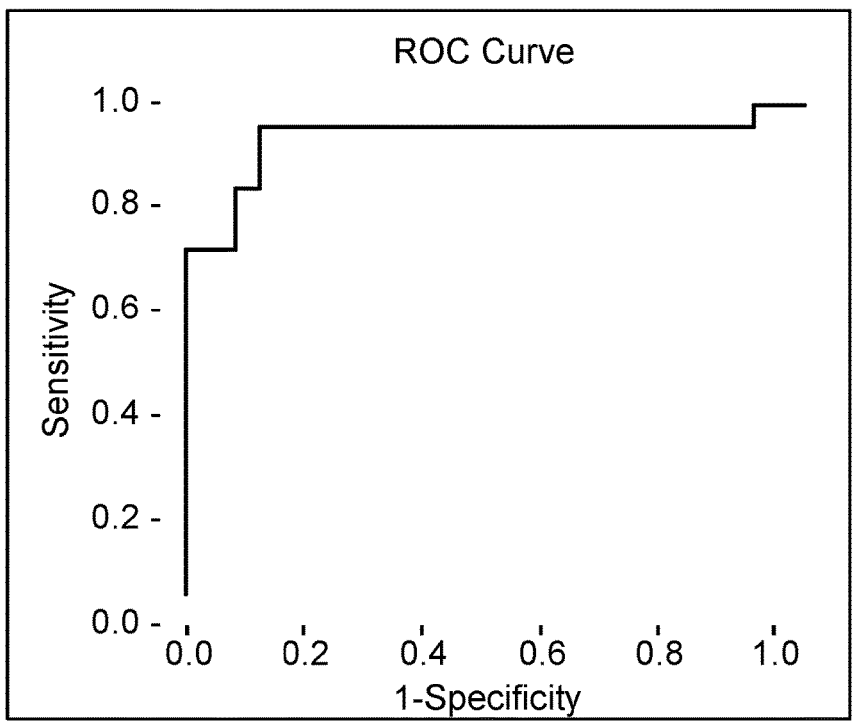
FIG. 12B shows a ROC curve illustrating the performance, using longitudinal ultrasound images, of a system for automatically diagnosing thyroid nodules implemented and trained in accordance with some embodiments of the disclosed subject matter.

FIGS. 12A and 12B shows a Receiver Operating Characteristic (ROC) curve illustrating the performance, using transverse and longitudinal ultrasound images, respectively, of a system for automatically diagnosing thyroid nodules implemented and trained in accordance with some embodiments of the disclosed subject matter. An example system for classifying images of nodules in B-mode US data implemented in accordance with some embodiments of the disclosed subject in which B-mode US images and mask information were used by an Inception V3-based CNN to automatically predict benign or malignant class membership of a thyroid nodule achieved 100% sensitivity (i.e., all malignant tumors were classified as being malignant, there were zero false negatives), and 52% specificity (i.e., 52% of benign nodules were properly classified as negative, while 48% of benign nodules were improperly classified as positive) on a test dataset of 50 nodules that included 25 benign nodules and 25 malignant nodules. Based on these results, a system implemented in accordance with some embodiments of the disclosed subject matter can indicate when a biopsy is not needed more than half the time, while being very unlikely to indicate that a biopsy is unnecessary when a nodule would be classified as malignant based on a fine needle aspiration biopsy. As described above, conventional techniques err on the side of performing biopsies, but only 9.2-13.0% of biopsies result in a diagnosis of a malignant nodule. Note that 100% of the nodules included in the test dataset were biopsied based at least in part on a human analysis of the B-mode US images in the test dataset. That is, conventional techniques based on expert analysis have a false positive rate that is relatively high, as around 90% of nodules that are biopsied via FNA are benign, which suggests a much higher than 48% false positive rate that was achieved with an automated nodule diagnosis system implemented in accordance with some embodiments of the disclosed subject matter.

FIG. 13 shows an example of various performance metrics based on outputs generated by systems for automatically diagnosing thyroid nodules implemented and trained in accordance with some embodiments of the disclosed subject matter. The results shown in FIG. 13 are based on different CNNs trained using images prepared differently. For example, the four columns under "InceptionV3" are results generated based on a CNN based on an InceptionV3 architecture that was trained from initialized values (i.e., the CNN was not pre-trained) using either whole labeled images (e.g., 256×256 pixel B-mode US images that included a nodule and that were labeled either benign or malignant based on the results of a biopsy of the nodule) in the "Image Only" columns, or an image and a mask (e.g., 256×256 pixel B-mode US images that included a nodule and that were labeled either benign or malignant based on the results of a biopsy of the nodule, and a corresponding mask indicating which pixels of the B-mode US image) in the "Image with Attention Map" columns.

For example, the four columns under "Resnet50" are results generated using a CNN based on a Resnet50 architecture that was trained using either whole labeled images (e.g., 256×256 pixel B-mode US images that included a nodule and that were labeled either benign or malignant based on the results of a biopsy of the nodule) in the "Image Only" columns, or an image and a mask (e.g., 256×256 pixel B-mode US images that included a nodule and that were labeled either benign or malignant based on the results of a biopsy of the nodule, and a corresponding mask indicating which pixels of the B-mode US image) in the "Image with Attention Map" columns.

The results are based on 600 retrospectively collected transverse and longitudinal B-mode US images depicting 150 benign and 150 malignant thyroid nodules from 300 patients (one nodule per patient) that were labeled based on a biopsy of the nodule. The dataset of 600 images was divided into a training dataset (230 patients corresponding to 460 images: 230 transverse and 230 longitudinal images corresponding to 115 benign nodules and 115 malignant nodules), a validation dataset (20 patients corresponding to 40 images: 20 transverse and 20 longitudinal images corresponding to 10 benign nodules and 10 malignant nodules), and a test dataset (50 patients corresponding to 100 images: 50 transverse and 50 longitudinal images corresponding to 25 benign nodules and 25 malignant nodules) on patient level such that the pair of images from a particular patient were either included or excluded from the training dataset. The images were resized to 256×256 pixels, and the nodules were manually segmented to generate a nodule mask. The nodule mask was provided on a second input channel to the CNNs to focus the attention of the network onto nodules during the training. Nodule masks were dilated by 10% of largest diameter to insure that surrounding tissue was included within the mask. The CNNs were trained and evaluated multiple times using the images with different preprocessing. For example, the CNNs were trained using masked images with only the nodule region provided as input to the CNN, whole images using an attention map (nodule mask) as a second channel input, and the whole image without an attention map. The training sets were consistent across the various CNNs. Image intensities were also scaled between 0 and 1 by dividing each pixel intensity value by the maximum intensity of 255. Saliency maps (shown in FIG. 14) were also generated by back propagating the gradients, which shows which pixels needed to be changed the least to affect the class score the most. As shown in FIG. 13, InceptionV3 using the nodule mask as a second input showed the best performance on the test dataset: 88% accuracy, 86% (sensitivity), 90% (specificity), 90% positive predictive value (PPV), and 82% negative predictive value (NPV). Note that the performance for the CNNs trained using the masked images with only the nodule region provided as input to the CNN exhibited poor performance (e.g., <20% sensitivity), and the results are not summarized in FIG. 13.

Figure 14C:
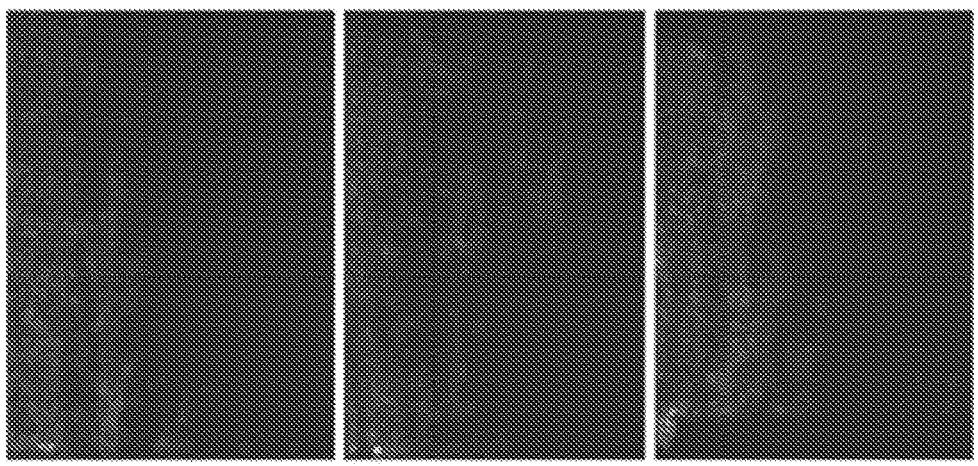
FIG. 14C shows examples of saliency maps generated from the B-mode ultrasound images shown in FIG. 14A based on a system for automatically diagnosing thyroid nodules implemented and trained using the whole ultrasound images in accordance with some embodiments of the disclosed subject matter.
Figure 14B:
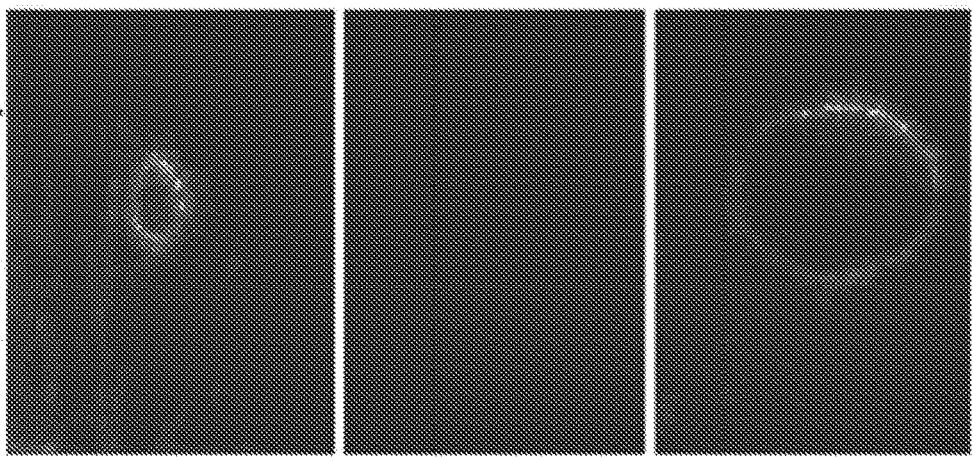
FIG. 14B shows examples of saliency maps generated from the B-mode ultrasound images shown in FIG. 14A based on a system for automatically diagnosing thyroid nodules implemented and trained using a mask indicating which portion of the ultrasound images correspond to a nodule in accordance with some embodiments of the disclosed subject matter.
Figure 14A:
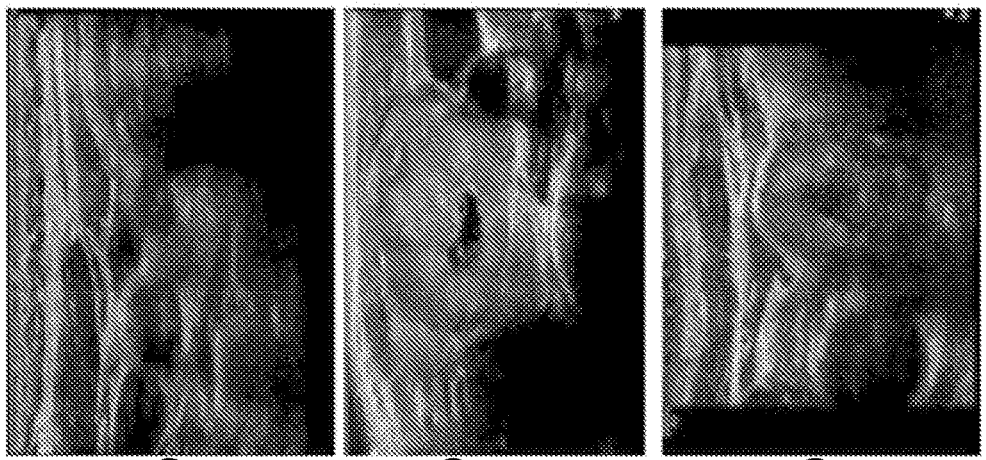
FIG. 14A shows examples of B-mode ultrasound images that depict a nodule.

FIG. 14A shows examples of B-mode ultrasound images that depict a nodule.

FIG. 14B shows examples of saliency maps generated from the B-mode ultrasound images shown in FIG. 14A based on a system for automatically diagnosing thyroid nodules implemented and trained using a mask indicating which portion of the ultrasound images correspond to a nodule in accordance with some embodiments of the disclosed subject matter.

FIG. 14C shows examples of saliency maps generated from the B-mode ultrasound images shown in FIG. 14A based on a system for automatically diagnosing thyroid nodules implemented and trained using the whole ultrasound images in accordance with some embodiments of the disclosed subject matter.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the processes of FIGS. 4 and 5 can be executed or performed in any order or sequence not limited to the order and sequence shown and described in the figures. Also, some of the above steps of the processes of FIGS. 4 and 5 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for automatically diagnosing thyroid nodules, the system comprising:
at least one hardware processor that is programmed to:
receive a B-mode ultrasound image of a subject's thyroid;
provide the B-mode ultrasound image to a first trained classification model, wherein the first trained classification model was trained to automatically segment B-mode ultrasound images input to the first trained classification model based on training data comprising manually segmented B-mode ultrasound images;
receive, from the first trained classification model, an output indicating which portions of the B-mode ultrasound image correspond to a nodule;
provide at least a portion of the B-mode ultrasound image corresponding to the nodule to a second trained classification model, wherein the second trained classification model was trained to automatically classify thyroid nodules based on manually labeled portions of B-mode ultrasound image data, color Doppler ultrasound image data, and shear wave elastography ultrasound image data corresponding to benign and malignant nodules; and
receive, from the second trained classification model, an output indicative of a likelihood that the nodule is malignant.

2. The system of claim 1, further comprising:
an ultrasound machine configured to output B-mode image data; and
the at least one hardware processor is further programmed to receive the B-mode ultrasound image from the ultrasound machine.

3. The system of claim 1, wherein the at least one hardware processor is further programmed to:
receive a color Doppler ultrasound image of the subject's thyroid;
provide at least a portion of the color Doppler ultrasound image corresponding to the nodule to the second trained classification model;
receive a shear wave elastography ultrasound image of the subject's thyroid;
provide at least a portion of the shear wave elastography ultrasound image corresponding to the nodule to the second trained classification model;
receive, from the second trained classification model, the output indicative of the likelihood that the nodule is malignant based on the information included in the B-mode ultrasound image, the color Doppler ultrasound image, and the shear wave elastography ultrasound image; and
concurrently provide at least the portion of the B-mode ultrasound image on a first input channel of the second trained classification model, at least the portion of the color Doppler ultrasound image on a second input channel of the second trained classification model, and at least the portion of the shear wave elastography ultrasound image on a third input channel of the second trained classification model.

4. The system of claim 3, wherein the at least one hardware processor is further programmed to:
automatically segment the shear wave elastography ultrasound image based on the segmentation of the B-mode ultrasound image.

5. The system of claim 1, wherein the at least one hardware processor is further programmed to:
receive, from the first trained classification model, a mask indicating which pixels of the B-mode ultrasound image correspond to the nodule.

6. The system of claim 1, wherein the second trained classification model is a convolutional neural network with an architecture based on Resnet 50.

7. The system of claim 1,
wherein the second trained classification model is configured to classify nodules into a first class and a second class, the first class corresponding to benign nodules and the second class corresponding to malignant nodules, and
wherein the at least one hardware processor is further programmed to:
indicate that the nodule is benign in response to a confidence value corresponding to a likelihood that the nodule is a member of the first class is indicative of a 100% confidence that the nodule is an example of the first class.

8. A method for automatically diagnosing thyroid nodules, the method comprising:
receiving a B-mode ultrasound image of a subject's thyroid;
providing the B-mode ultrasound image to a first trained classification model, wherein the first trained classification model was trained to automatically segment B-mode ultrasound images input to the first trained classification model based on training data comprising manually segmented B-mode ultrasound images;
receiving, from the first trained classification model, an output indicating which portions of the B-mode ultrasound image correspond to a nodule;
providing at least a portion of the B-mode ultrasound image corresponding to the nodule to a second trained classification model, wherein the second trained classification model was trained to automatically classify thyroid nodules based on manually labeled portions of B-mode ultrasound image data, color Doppler ultrasound image data, and shear wave elastography ultrasound image data corresponding to benign and malignant nodules; and
receiving, from the second trained classification model, an output indicative of a likelihood that the nodule is malignant.

9. A system for automatically diagnosing thyroid nodules, the system comprising:
at least one hardware processor that is programmed to:
receive a B-mode ultrasound image of a subject's thyroid;
receive information indicating which portions of the B-mode ultrasound correspond to a nodule;
provide at least a portion of the B-mode ultrasound image corresponding to the nodule to a trained classification model, wherein the trained classification model was trained to automatically classify thyroid nodules based on training data comprising a plurality of B-mode ultrasound images and at least one of a plurality of Doppler ultrasound images or a plurality of shear wave elastography ultrasound images each labeled as including a benign nodule or a malignant nodule; and
receive, from the trained classification model, an output indicative of a likelihood that the nodule is malignant.

10. The system of claim 9, wherein the at least one hardware processor is further programmed to:
provide at least the portion of the B-mode ultrasound image on a first input channel of the trained classification model, and the information indicating which portions of the B-mode ultrasound correspond to the nodule on a second input channel of the trained classification model.

11. The system of claim 9, wherein the information indicating which portions of the B-mode ultrasound correspond to the nodule comprises a mask indicating which pixels of the B-mode ultrasound image correspond to the nodule.

12. The system of claim 11, wherein the at least one hardware processor is further programmed to:
provide the mask as an input to the trained classification model.

13. The system of claim 9, wherein the at least one hardware processor is further programmed to:
provide the B-mode ultrasound image to a first trained classification model, wherein the first trained classification model was trained to automatically segment B-mode ultrasound images based on manually segmented B-mode ultrasound images; and
receive, from the first trained classification model, the mask.

14. The system of claim 9, wherein the trained classification model is a convolutional neural network with an architecture based on Resnet 50.

15. The system of claim 9, wherein the trained classification model is a convolutional neural network with an architecture based on InceptionV3.

16. The system of claim 9, wherein the trained classification model is configured to classify nodules into a first class and a second class, the first class corresponding to benign nodules and the second class corresponding to malignant nodules.

17. The system of claim 16, wherein the output of the trained classification model comprises a first confidence value corresponding to a likelihood that the nodule is a member of the first class, and a second confidence value corresponding to a likelihood that the nodule is a member of the second class.

18. The system of claim 17, wherein the at least one hardware processor is further programmed to:
indicate that the nodule is benign in response to the first confidence value corresponding to a 100% confidence that the nodule is a member of the first class.

19. The system of claim 9, wherein the at least one hardware processor is further programmed to:
receive a longitudinal B-mode ultrasound image of the subject's thyroid;
receive information indicating which portions of the longitudinal B-mode ultrasound correspond to the nodule;
provide at least a portion of the longitudinal B-mode ultrasound image to the trained classification model; and
receive, from the trained classification model, a second output indicative of a likelihood that the nodule is malignant.

20. The system of claim 19, wherein the at least one hardware processor is further programmed to:
indicate that the nodule is benign in response to the output and the second output both indicating with 100% confidence that the nodule is benign.

* * * * *